United States Patent
Chodorowski-Kimmes

(10) Patent No.: US 10,973,751 B2
(45) Date of Patent: Apr. 13, 2021

(54) HAIR DYEING PROCESS COMPRISING A PIGMENT AND AN AQUEOUS DISPERSION OF SUPRAMOLECULAR POLYMER

(71) Applicant: L'OREAL, Paris (FR)

(72) Inventor: Sandrine Chodorowski-Kimmes, Aulnay-Sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/500,496

(22) PCT Filed: Apr. 9, 2018

(86) PCT No.: PCT/EP2018/059026
§ 371 (c)(1),
(2) Date: Oct. 3, 2019

(87) PCT Pub. No.: WO2018/185335
PCT Pub. Date: Oct. 11, 2018

(65) Prior Publication Data
US 2020/0108007 A1    Apr. 9, 2020

(30) Foreign Application Priority Data
Apr. 7, 2017 (FR) ..................... 1753078

(51) Int. Cl.
*A61Q 5/10*    (2006.01)
*A61K 8/81*    (2006.01)
*A61K 8/46*    (2006.01)
*A61Q 5/06*    (2006.01)

(52) U.S. Cl.
CPC ........... *A61K 8/8194* (2013.01); *A61K 8/463* (2013.01); *A61Q 5/065* (2013.01); *A61K 2800/43* (2013.01)

(58) Field of Classification Search
CPC .... A61Q 5/10; A61Q 5/065; A61K 2800/432; A61K 8/4906; A61K 8/8194; A61K 2800/43
USPC .............................................................. 8/405
See application file for complete search history.

(56) References Cited

U.S. PATENT DOCUMENTS

| 2010/0154134 A1* | 6/2010 | Brun ................... C08K 5/0041 8/405 |
| 2015/0082554 A1* | 3/2015 | Allard .................... A61K 8/31 8/408 |
| 2015/0139925 A1* | 5/2015 | Kamikawa ............. A61K 8/86 424/62 |

FOREIGN PATENT DOCUMENTS

EP    2 189 148 A2    5/2010

OTHER PUBLICATIONS

STIC Search Report dated Aug. 13, 2020.*
International Search Report dated Jun. 6, 2018 in PCT/EP2018/059026 filed on Apr. 9, 2018.

* cited by examiner

*Primary Examiner* — Eisa B Elhilo
(74) *Attorney, Agent, or Firm* — Oblon, McClelland, Maier & Neustadt, L.L.P.

(57) ABSTRACT

The present invention relates to a hair dyeing process comprising at least one pigment and at least one aqueous dispersion of polyalkene supramolecular polymer with a surfactant system chosen from an anionic surfactant, a cationic surfactant and a non-ionic surfactant.

25 Claims, No Drawings

HAIR DYEING PROCESS COMPRISING A PIGMENT AND AN AQUEOUS DISPERSION OF SUPRAMOLECULAR POLYMER

The present invention relates to a hair dyeing process comprising a pigment and an aqueous dispersion of supramolecular polymer, a composition comprising the pigment and said dispersion.

The supramolecular polymers are interesting in the cosmetic field, particularly for make-up products, skincare products or hair products, for their film-forming properties exhibiting good hold and non-transfer of the deposit during contact with clothing or a glass.

In application EP-A-2189151, make-up compositions are known containing a polymer of polycondensate type containing polyalkene polymer, diisocyanate and a compound with a supramolecular group like the group ureidopyrimidone. However, such a polymer is soluble in hydrocarbon organic solvents like isododecane and is therefore difficult to incorporate in aqueous cosmetic compositions such as shampoos, aqueous gels (for example care compositions in the form of serum) and aqueous emulsions. What is more, after spreading and evaporation of the organic solvent, this polymer in organic solution gives a film that exhibits a tacky appearance.

In the keratin fibre dyeing field, it is already known to dye keratin fibres by various techniques using direct dyes for non-permanent colourings or dye precursors for permanent colourings.

Non-permanent dyeing or direct dyeing consists in dyeing the keratin fibres with dyeing compositions containing direct dyes. These dyes are coloured and colouring molecules which have an affinity for keratin fibres. They are applied to the keratin fibres for a period of time required to obtain the desired colouring, then rinsed off.

The conventional dyes which are used are in particular dyes of the nitrobenzene, anthraquinone, nitropyridine, azo, xanthene, acridine, azine or triarylmethane type or natural dyes.

Some of these dyes can be used under lightening conditions, thereby making it possible to obtain visible colourings on dark hair.

It is also known to dye keratin fibres permanently by means of oxidation dyeing. This dyeing technique consists in applying to the keratin fibres a composition containing dye precursors such as oxidation bases and couplers. These precursors, under the action of an oxidizing agent, will form one or more coloured species in the hair.

The variety of molecules involved in terms of oxidation bases and couplers makes it possible to obtain a rich range of colours and the colourings which result therefrom are generally permanent, powerful and resistant to external agents, in particular to light, to bad weather, to washing, to perspiration and to rubbing.

In order to be visible on dark hair, these dyeing techniques require prior or simultaneous bleaching of the keratin fibres. This bleaching step carried out with an oxidizing agent such as hydrogen peroxide or persalts causes not insignificant damage to the keratin fibres, thereby impairing their cosmetic properties. The hair then has a tendency to become rough, more difficult to disentangle and more brittle. Another dyeing method consists in using pigments. Specifically, the use of a pigment at the surface of keratin fibres makes it possible in general to obtain visible colourings on dark hair since the surface pigment masks the natural colour of the fibre. The use of pigment to dye keratin fibres is, for example, described in Patent Application FR 2 741 530, which recommends the use, for the temporary dyeing of keratin fibres, of a composition comprising at least one dispersion of film-forming polymer particles comprising at least one acid function and at least one pigment dispersed in the continuous phase of said dispersion.

The colourings obtained by means of this method of dyeing have the drawback of being removed as soon as the hair is shampooed for the first time.

It is, moreover, known from Patent Application FR 2 907 678 to carry out coloured coatings of the hair using a composition comprising a polysiloxane/polyuria block copolymer and a pigment. However, with such a composition, the coatings obtained are not always very uniform and the individualization of the hairs is not always very good.

It is also known from Patent EP 1 392 222 to use a cosmetic composition for caring for and/or treating keratin materials comprising a supramolecular polymer comprising a polymeric backbone and at least two groups capable of forming at least three hydrogen bonds, and from Patent EP 1 435 900 to use a hair composition comprising a supramolecular polymer comprising a polymeric backbone and at least two groups capable of forming at least three hydrogen bonds and a surfactant or a hair-conditioning agent.

Thus, the aim of the present invention is to provide a composition for dyeing keratin fibres, such as the hair, which makes it possible to obtain coloured coatings which have good resistance to attacks such as brushing, which do not bleed, which are resistant to sweat, to light and to bad weather, and which are resistant to shampooing and to the various attacks to which the hair might be subjected, without damaging the keratin fibres and while at the same time preserving perfectly individualized hairs.

A subject of the present invention is a hair dyeing process comprising at least one pigment and at least one aqueous dispersion of a polyalkene supramolecular polymer with a specific surfactant system as described hereinafter and in claim 1.

Another subject of the invention is a composition comprising at least one pigment and at least one aqueous dispersion as described previously.

The aqueous dispersion of polymer is presented in the form of a dispersion of polymer particles in water. The size of the polymer particles in dispersion in the aqueous phase may range from 5 nm to 600 nm, and preferably from 80 nm to 400 nm.

In the sense of the present invention, polyalkene supramolecular polymer is understood to mean a polymer including in its structure at least one polyalkene portion and at least one portion including at least one group that can form at least three hydrogen bonds, preferably four hydrogen bonds.

The supramolecular polymers of the invention may especially be from the condensation of at least one polyalkene polymer (A) functionalized by at least one reactive group, with at least one functionalized graft (B) by at least one reactive group that can react with the reactive group or groups of the functionalized polyalkene polymer, said graft bearing at least one group that can form at least three hydrogen bonds, preferably four hydrogen bonds.

Preferably, the functionalized polyalkene polymer (A) has formula A1:

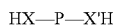

where XH and X'H are reactive groups, with X and X', which may be identical or different, chosen from O, S, NH and $NR_a$, $R_a$ representing a linear or branched $C_1$-$C_6$ alkyl group;

P represents a homo- or copolymer that can be obtained by polymerization of one or more linear, cyclic and/or branched, mono- or polyunsaturated $C_2$-$C_5$ alkenes.

P preferably represents a polyethylene, a polybutylene, a polybutadiene, a hydrogenated polybutadiene, a polyisoprene, a poly(1,3-pentadiene), a polyisobutylene, and their copolymers such as poly(ethylenebutylene), preferably a hydrogenated polybutadiene.

Poly(ethylene/butylenes) are copolymers of 1-butene and of ethylene. They may be represented schematically by the following sequence of units: [—CH$_2$—CH$_2$-] and [—CH$_2$CH(CH$_2$—CH$_3$)—]

The polybutadienes may be 1,4-polybutadienes or 1,2-polybutadienes, which may be represented schematically, respectively, by the following sequences of units:
[—CH$_2$—CH=CH—CH$_2$—] (1,4-polybutadienes)
[—CH$_2$—CH(CH=CH$_2$)—] (1,2-polybutadienes)

Preferably, they are 1,2-polybutadienes.

Polyisoprenes may be represented schematically by the following sequences of units:

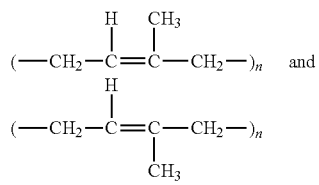
and

A mixture of above units may obviously also be used, so as to form copolymers.

The functionalized polyalkene polymer is preferably functionalized at the end of the chain. They are then referred to as telechelic polymers.

Preferably, the functionalized polyalkene polymers have a number-average molecular mass (Mn) of greater than or equal to 1000, especially between 1000 and 5000, or even between 1500 and 3500.

The functionalized polyalkene polymers may be totally hydrogenated to avoid the risks of crosslinking.

Preferably, for the polyalkene polymer HX—P—X'H, X and X' are identical. Particularly X=X'=O.

Among the preferred HX—P—X'H polyalkene polymers, mention may be made of polydienes, which are preferably hydrogenated, containing hydroxyl functions, preferably hydroxyl end groups, and polyolefins containing hydroxyl end groups.

The polydienes containing hydroxyl end groups are especially defined, for example, in FR 2 782 723. They may be chosen from polybutadiene, polyisoprene and poly(1,3-pentadiene) homopolymers and copolymers. Preferably, they have a number-average molecular mass (Mn) of less than 7000, preferably between 1000 and 5000; and present functionality at the hydroxyl ends of 1.8 to 3, and preferably in the region of 2. Mention will be made in particular of the hydroxylated polybutadienes sold by the company Cray Valley under the brand names Poly BD R-45HT and Poly BD R-20 LM, which will preferably be used hydrogenated; and also hydrogenated dihydroxylated (1,2-polybutadienes), such as GI3000 of Mn=3100, GI2000 (Mn=2100) and GI1000 (Mn=1500) sold by the company Nisso.

Among the polyolefins with hydroxyl end groups, mention may be made preferably of polyolefins, homopolymers or copolymers with am-hydroxyl end groups, such as polyisobutylenes with am-hydroxyl end groups; and the copolymers having formula:

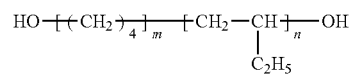

especially those sold by Mitsubishi under the brand name Polytail.

The supramolecular polymers of the present invention have in their structure at least one graft bearing at least one group that can form at least three hydrogen bonds, preferably at least four hydrogen bonds.

The groups that can form at least three hydrogen bonds may comprise for example at least three functional groups, preferably at least four functional groups, chosen from:

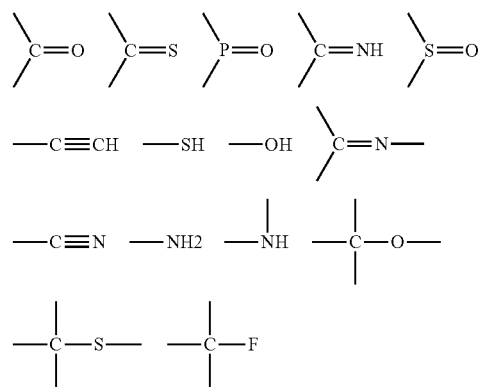

These functional groups may be classified into two categories:

hydrogen bond donor functional groups such as the groups:

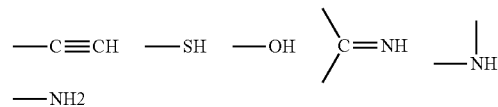

and hydrogen bond acceptor functional groups such as the groups:

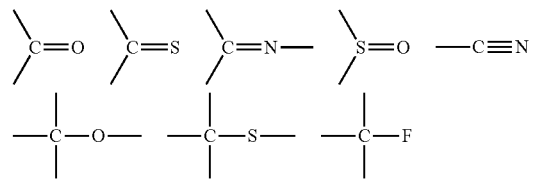

The groups that can form at least three hydrogen bonds form a basic structural element including at least three groups, preferably at least four groups and more preferably four functional groups capable of establishing hydrogen bonds. The basic structural elements capable of establishing three or four hydrogen bonds may be represented schematically in the following manner:

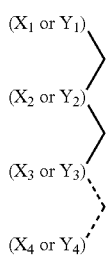

where $X_i$ (i is a natural integer) is a hydrogen bond acceptor functional group and $Y_i$ is a hydrogen bond donor functional group.

Thus, each structural element should be capable of establishing hydrogen bonds with one or more partner structural elements, which are identical (i.e. self-complementary) or different, such that each pairing of two partner structural elements takes place by the formation of at least three hydrogen bonds, preferably at least four hydrogen bonds and more preferably four hydrogen bonds.

A proton acceptor X will pair with a proton donor Y.

Several possibilities are thus offered, for example pairing of:
XXXX with YYYY;
XXXY with YYYX;
XXYX with YYXY;
XYYX with YXXY;
XXYY with YYXX self-complementary or otherwise;
XYXY with YXYX self-complementary or otherwise.

Preferably, the groups may establish four hydrogen bonds with an identical (or self-complementary) partner group among which are two donor bonds (for example NH) and two acceptor bonds (for example CO and —C=N—).

Preferably, the groups that can form at least three hydrogen bonds include 5- or 6-membered rings (aromatic rings or unsaturated heterocycles) very often constituted of C and/or N atoms and with conjugated double bonds to stabilize and direct the hydrogen interactions.

Even more preferably, the groups that can form at least three hydrogen bonds are part of 6-membered rings comprising C and/or N atoms and with conjugated double bonds to stabilize and direct the hydrogen interactions.

According to a specific embodiment of the invention, the groups that can form at least three or four hydrogen bonds are chosen from the following families, it being understood that all the tautomeric forms are included:

(i) aminopyrimidones having formula:

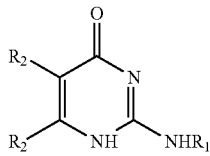

(ii) ureidopyrimidones having formula:

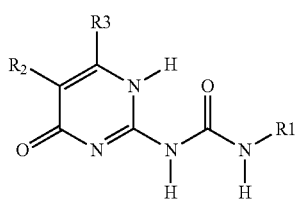

(iia) imidazolidones having formula:

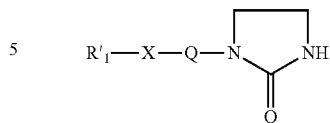

in which:
Q denotes a divalent hydrocarbon substituent having from 1 to 10 carbon atoms, optionally interrupted by a —COO— —OCO—, —CO—, —O—, —S—, —NH—, —CONH— group; X denotes a divalent nucleophilic group chosen from —NH—, —$NR_b$—, —O—, —S—, —OOC—; Rb denotes a $C_1$-$C_4$ alkyl group;

R'1 denotes a single bond constituting the connection point on the rest of the graft.

(iii) acylaminopyridines and especially:
monoacylaminopyridines having structure:

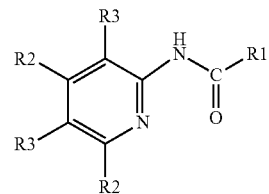

di(acylamino)pyridines and more particularly 2,6-di(acylamino)pyridines having structure:

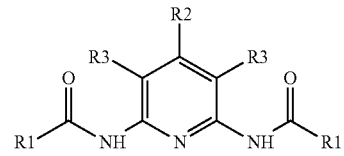

(iv) aminopyrimidines, and especially:
aminopyrimidine compounds:

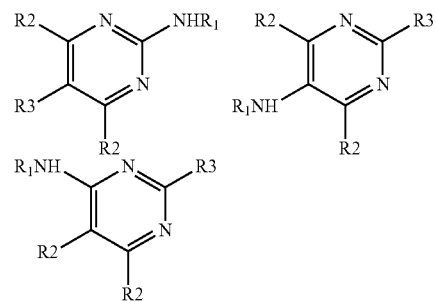

diaminopyrimidine compounds having structure:

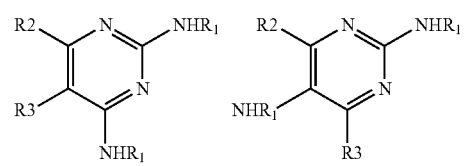

-continued

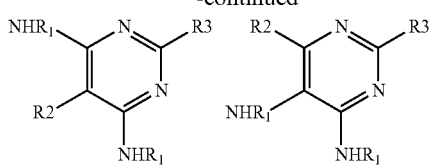

triaminopyrimidine compounds;

(v) ureidotriazines, and especially mono-, di- and tri-ureidotriazines, and in particular ureidoaminotriazines having structure:

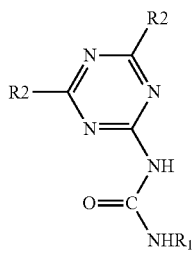

(vi) (acylamino)triazines and especially mono-, di- and tri-acylamino triazines, optionally amino (mono-, di- or triamino), in particular:

di(acylamino)triazines having structure:

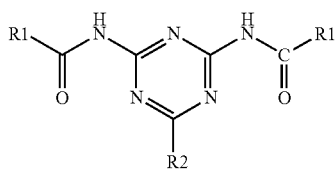

acylamino, amino-triazines, (mono- or diacylamino, and mono- or diamino) and especially compounds having structure:

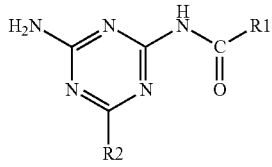

acylaminotriazines having structure:

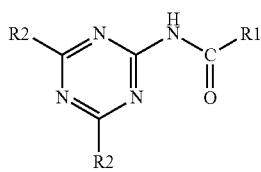

tri-acylaminotriazines;

(vii) aminotriazines, and especially:
monoaminotriazines;
2,6-diamino-s-triazines having structure:

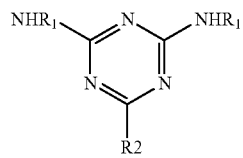

triamino-s-triazine compounds having structure:

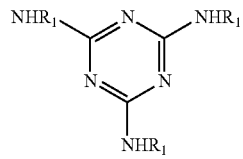

(viii) acylaminotriazoles having structure:

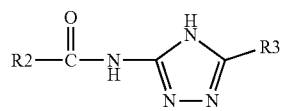

(ix) compounds of the urazoylbenzoic acid family having structure:

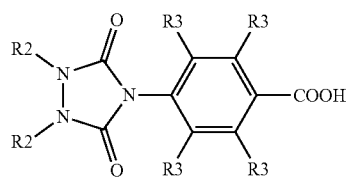

(x) phthalhydrazides having structure:

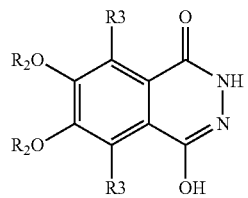

(xi) uracils having structure:

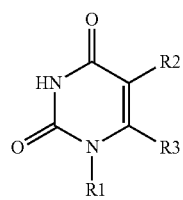

(xii) thymines having structure:

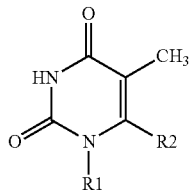

(xiii) succinimides having structure:

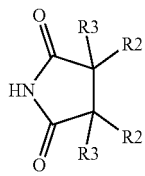

(xiv) glutarimides having structure:

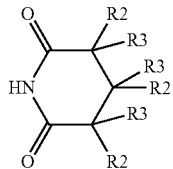

(xv) compounds of the cyanuric acid family having structure:

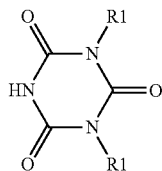

(xvi) maleimides:

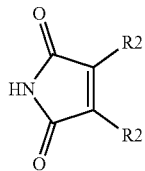

(xvii) compounds of the barbituric acid family, having structure:

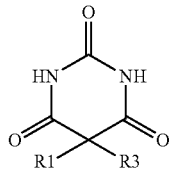

(xviii) compounds having structure:

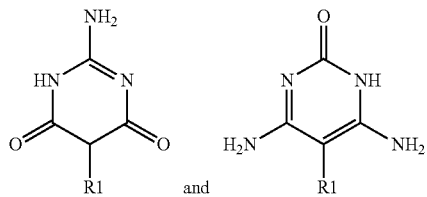

and (xix) compounds of the trimellitic acid family, having formula:

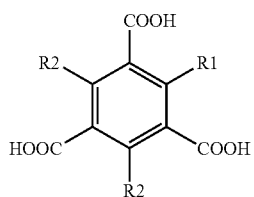

(xx) ureidopyridines, especially mono- or di-ureidopyridines, and in particular those having formula:

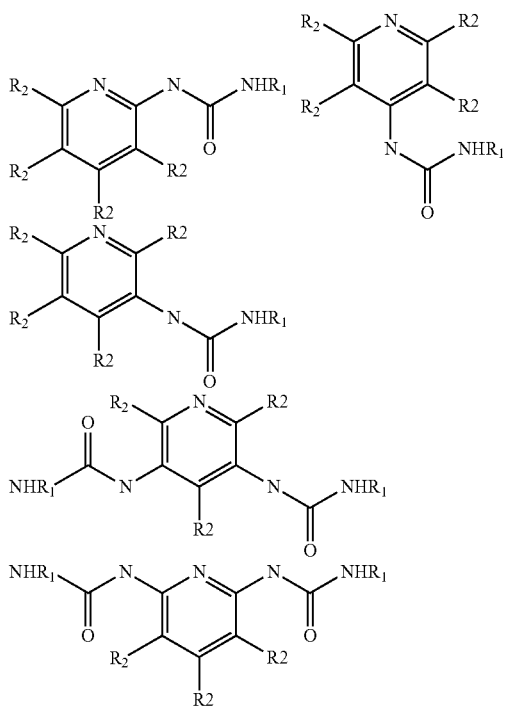

(xxi) carbamoylpyridines having formula:

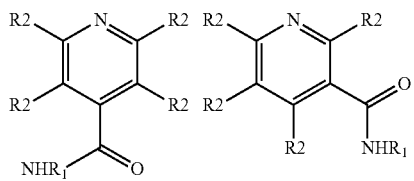

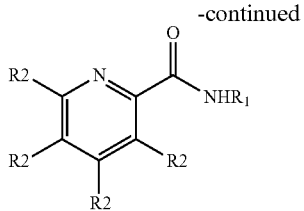

(xxii) adenines having formula:

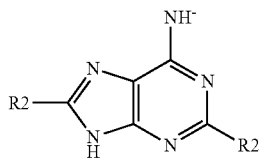

(xxiii) guanines having formula:

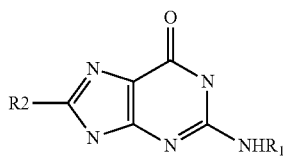

(xxiv) cytidines having formula:

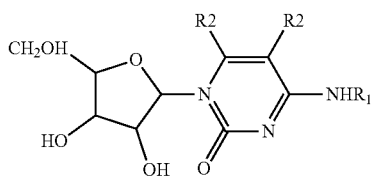

In all of these formulae, the substituents have the following meanings:

(a) the substituents $R_1$, which may be identical or different, represent a single bond, a hydrogen atom, a halogen atom and/or a linear, branched or cyclic, $C_1$-$C_{6000}$, saturated or unsaturated, optionally aromatic monovalent carbon-based group (especially alkyl), which may contain one or more heteroatoms such as O, S, N, P, Cl, Br, F; or a combination of these meanings.

The substituent $R_1$ may especially be a $C_4$-$C_{12}$ cycloalkyl group, a linear or branched $C_1$-$C_{30}$ alkyl group or a $C_4$-$C_{12}$ aryl group, optionally substituted with an amino, ester and/or hydroxyl function.

The substituent $R_1$ may also be a group: $C_4H_9$, phenyl, 1,4-nitrophenylene, 1,2-ethylene, 1,6-hexylene; 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), -isophorone-, 4,4'-methylene bis(cyclohexylene), tolylene, 2-methyl-1,3-phenylene, 4-methyl-1,3-phenylene, 4,4-biphenylenemethylene, and preferably: -isophorone-, —$(CH_2)_2$—, —$(CH_2)_6$—, $CH_2CH(CH_3)$—$CH_2$—$C(CH_3)_2$—$CH_2$—$CH_2$, 4,4'-methylene biscyclohexylene, 2-methyl-1,3-phenylene.

Even more preferably, $R_1$ is a single bond.

(b) the substituents $R_2$, which may be identical or different within the same formula, represent a single bond, a hydrogen atom, a halogen atom (—Br, —Cl, —F), a —OH, —N(R)$_2$ substituent (with R being H or a linear and branched $C_1$-$C_{12}$ and preferably a $C_1$-$C_4$ alkyl substituent, and better still a methyl or ethyl substituent); or a linear, branched or cyclic, $C_1$-$C_{6000}$, saturated or unsaturated, optionally aromatic monovalent hydrocarbon-based group, which may contain one or more heteroatoms such as O, S, N, P and F; or a combination of these meanings.

The substituents $R_2$ may especially be H, CN, NH$_2$ or:

a $C_1$-$C_{30}$ alkyl group;

a $C_4$-$C_{12}$ cycloalkyl group;

a $C_4$-$C_{12}$ aryl group;

a ($C_4$-$C_{12}$)aryl($C_1$-$C_{30}$)alkyl group;

a $C_1$-$C_4$ alkoxy group;

an arylalkoxy group, in particular an aryl($C_1$-$C_4$)alkoxy group;

a $C_4$-$C_{12}$ heterocycle;

a thioalkoxy group;

a sulfoxy group;

or mixtures thereof, these groups optionally being substituted with an amino, ester and/or hydroxyl function.

Preferably, $R_2$ represents H, $CH_3$, $C_{13}H_{27}$, $C_7H_{15}$ or phenyl.

(c) the substituents $R_3$, which may be identical or different within the same formula, represent a hydrogen atom or a linear, branched or cyclic, $C_1$-$C_{6000}$, saturated or unsaturated, optionally aromatic monovalent hydrocarbon-based group, which may contain one or more heteroatoms such as O, S, N, P or F; or a combination of these meanings.

The substituent $R_3$ may especially be a $C_4$-$C_{12}$ cycloalkyl group, a linear or branched $C_1$-$C_{30}$ alkyl group or a $C_4$-$C_{12}$ aryl group, optionally substituted with an amino, ester and/or hydroxyl function. Preferably, substituent $R_3$ represents a methyl substituent. In all of these formulae, it is clearly understood that at least one, especially one or two, of the groups $R_1$ and/or $R_2$ is a single bond constituting the point of attachment of the group that can form at least three hydrogen bonds to the rest of the graft.

Preferably, said point of attachment is borne by $R_1$ and/or $R_2$, and preferably it is borne by $R_1$.

The groups that can form at least three hydrogen bonds are chosen especially from: (a) groups that can form at least three complementary and identical hydrogen bonds, i.e. self-complementary, and especially:

aminopyrimidones, ureidopyrimidones, imidazolidones, compounds of the trimellitic acid family, or of the urazoylbenzoic acid family, acylaminopyridines, ureidopyridines, carbamoylpyridines, acylaminotriazines, ureidotriazines, and especially ureidoaminotriazines, diaminotriazines, acylaminotriazoles, phthalhydrazides, compounds having formula:

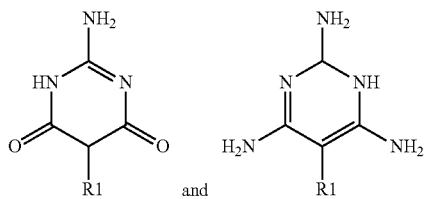

in which R₁ is a hydrogen atom or a linear, branched or cyclic, $C_1$-$C_{6000}$, saturated or unsaturated, optionally aromatic monovalent hydrocarbon-based group, which may contain one or more heteroatoms such as O, S, N, P and F, (b) groups that can form at least three complementary but different hydrogen bonds and especially:

adenine, which is complementary to guanine,
cytidine, which is complementary to thymine,
triamino-s-triazine, which is complementary to uracil or succinimide or glutarimide or cyanuric acid or thymine or maleimide or (di)aminopyrimidine or barbituric acid,
acylamino-amino-s-triazine, which is complementary to uracile or succinimide or glutarimide or cyanuric acid or thymine or maleimide or (di)aminopyrimidine or barbituric acid.

In a preferred manner, the groups that can form at least three hydrogen bonds are chosen from groups that can establish at least three hydrogen bonds with themselves (self-complementary), especially at least four hydrogen bonds with themselves. Among these groups, mention may be made in particular of:

ureidopyrimidones; imidazolidones;
ureidopyridines, carbamoylpyridines;
acylamino-s-triazines and especially acyl-diamino-s-triazines;
ureidotriazines;
phthalhydrazides;
compounds having formula:

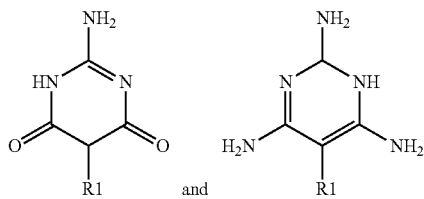

in which the substituents R₁, R₂ and R₃ have the meanings given above, in particular the meanings given as a preference.

Better still, as preferred examples of groups that can form at least three hydrogen bonds, mention may be made of groups derived from ureidopyrimidones and imidazolidines, preferably groups derived from ureidopyrimidones and in particular from 2-ureidopyrimidone or 6-methyl-2-ureidopyrimidone.

The rest of the functionalized graft is constituted of a linker L bearing at least one reactive group (W) that can react with the reactive group or groups of the functionalized poly(alkene).

This reactive group (W) may be for example a carboxyl group or an isocyanate group. Preferably, it is a —N═C═O or —N═C═S group, and even more preferably, a —N═C═O group (isocyanate).

Preferably, linker L is a divalent saturated or unsaturated C2-C20, preferably C6-C20 hydrocarbon-based substituent. Preferably, linker L is a divalent saturated or unsaturated cyclic $C_6$-$C_{20}$, preferably $C_6$-$C_{12}$ hydrocarbon-based substituent. A divalent cyclic hydrocarbon-based substituent is understood to mean a substituent containing in its structure at least one cyclic portion.

Linker L may be a divalent substituent chosen from phenylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), -isophorone-, 4,4'-methylene bis(cyclohexylene), tolylene, 2-methyl-1,3-phenylene, 4-methyl-1,3-phenylene, 4,4-biphenylenemethylene. L preferably represents a divalent group: phenylene, -isophorone-, 4,4'-methylene biscyclohexylene, tolylene, 2-methyl-1,3-phenylene, 4-methyl-1,3-phenylene, 4,4-biphenylenemethylene, and preferably -isophorone-, 4,4'-methylene biscyclohexylene, 2-methyl-1,3-phenylene.

Preferably, L is the divalent group -isophorone-.

Divalent isophorone group is understood to mean the following group:

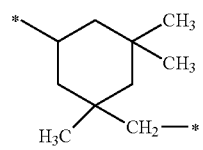

representing the attachment points for the group in the polymer backbone.

In a particularly preferred version of the invention, the functionalized grafts (B) have formula (B1):

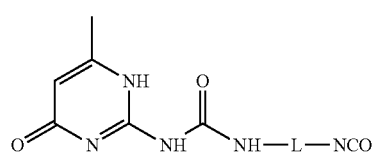

(B1)

or have the formula (B2):

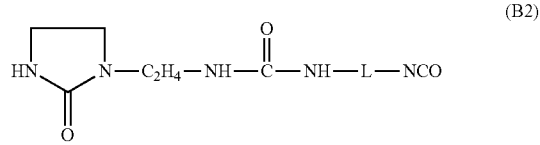

(B2)

Where L has the same meaning as above.

Even more preferably, the polyalkene supramolecular polymer has formula (C1):

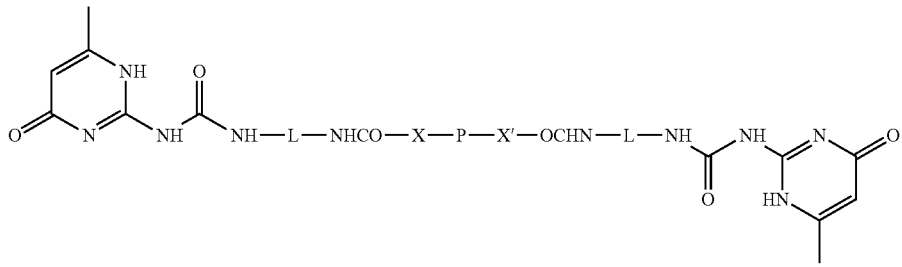

P, X, X', L having the meanings indicated previously.
or having formula (C2):

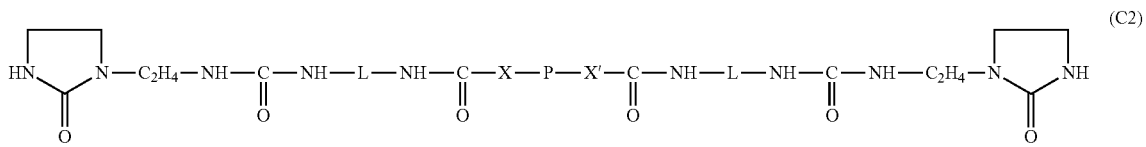

P, X, X', L having the meanings indicated previously.

Preferably, X=X'=O.

Preferably, in formulas (C1), (C2), X and X' denote an oxygen atom.

The polyalkene supramolecular polymer or polymers of the invention may also be obtained from a polymer (A1) including a polyalkene portion, said polymer being functionalized by at least one reactive group (B1), which reacts by condensation with at least one molecule (A2) including at least one reactive group (B2), said molecule being such that after reaction of groups (B1) and (B2) an entity forms that can form at least three hydrogen bonds, preferably at least four hydrogen bonds.

Preferably, these entities are structures (i) to (xxiv) as defined previously, with $R_1$ denoting a single bond.

Polymer (A1) may especially result from the action on a functionalized polyalkene polymer having formula A as defined before, of compounds (A2) including two reactive groups (B2) and (B'2) that can react with the functionalized groups of the polyalkene.

These reactive groups may for example be carboxyl groups or isocyanate groups. Preferably, it is —N=C=O or —N=C=S groups, and even more preferably an —N=C=O group (isocyanate).

Preferably, B2 groups are identical to B'2 groups.

Preferably, the compounds (A2) have the following structure (C'):

B'2-L-B'2  (C')

where linker L has the same meanings as those defined previously.

In a particularly preferred version of the invention, the polymers A1 have formula (C'1):

CON-L-NCO—X—P—X'—CON-L-NCO  (C'1)

in which L, X, X' and P have the same meanings as those described previously.

Preferably, molecule (A2) is 6-methylisocytosine having formula:

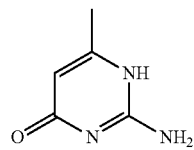

or 2-aminoethylimidazolidine (UDETA) having formula:

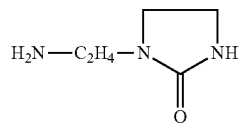

In practice, the polyalkene supramolecular polymer may be prepared according to a preparation process consisting in:
heating polymer (A1) including at least one reactive group, especially two reactive groups, particularly two OH groups, to a temperature that can be inclusively between 60° C. and 140° C., ensuring in advance that the polymer does not include residual water.
adding at least one, preferably only one, functionalized graft by at least one reactive group that can react with the reactive group or groups on the functionalized polyalkene polymer;
stirring the mixture under a controlled atmosphere at a temperature of the order of 90-130° C.; for 1 to 24 hours;
monitoring reaction progress for example by assaying the reactive groups borne by the polymer (for example by finding the hydroxyl indices if the polymer bears hydroxyl groups) and/or by monitoring the disappearance of the reactive groups borne by the graft or grafts (for example by monitoring by infrared spectroscopy the disappearance of the characteristic isocyanate band between 2500 and 2800 cm$^{-1}$ so as to stop the reaction when the peak completely disappears)

letting the finished product return to ambient temperature;

optionally adding a compound G-XH and/or G-X'H to ensure the complete disappearance of the reactive groups borne by the graft; G denotes a hydrogen atom or a C1-C12 linear or branched alkyl substituent; particularly, X, X' being as defined previously, GXH denotes the ethanol if the graft bears isocyanate functions;

filtering the mixture if necessary.

The reaction may be performed in the presence of a solvent or a mixture of solvents, in particular chosen from methyltetrahydrofuran, tetrahydrofuran, toluene or butyl acetate, or propylene carbonate.

It is also possible to add a conventional catalyst to achieve the condensation between the functionalized polymer and the functionalized graft.

The resulting compound may finally be washed and dried, or even purified, according to the general knowledge of those skilled in the art.

According to a preferred embodiment, the polyalkene supramolecular polymer may be prepared according to a preparation process consisting in:

heating the polyalkene polymer that is di-functionalized by hydroxyl functions (preferably functionalized at the ends of the chain) (polymer A1) at a temperature that can be comprised between 60° C. and 140° C., ensuring previously that it does not include residual water;

adding a functionalized isocyanate, preferably diisocyanate, graft.

stirring the mixture under a controlled atmosphere at a temperature of the order of 90-130° C.; for 1 to 24 hours;

monitoring reaction progress for example by assaying the reactive groups borne by the polymer (for example by finding the hydroxyl indices if the polymer bears hydroxyl groups) and/or by monitoring the disappearance of the reactive groups borne by the graft or grafts (for example by monitoring by infrared spectroscopy the disappearance of the characteristic isocyanate band between 2500 and 2800 cm$^{-1}$ so as to stop the reaction when the peak completely disappears)

letting the finished product return to ambient temperature;

optionally a compound G-XH and/or G-X'H to ensure the complete disappearance of the reactive groups borne by the graft; G denotes a hydrogen atom or a C1-C12 linear or branched alkyl substituent; X and X' being as defined previously (preferably denote O); in particular, GXH and GX'H denote the ethanol if the graft bears isocyanate functions;

filtering the mixture if necessary.

The reaction may be performed in the presence of a solvent or a mixture of solvents, in particular chosen from methyltetrahydrofuran, tetrahydrofuran, toluene or butyl acetate, or propylene carbonate.

It is also possible to add a conventional catalyst to achieve the condensation between the functionalized polymer and the functionalized graft. As an example, mention may be made of dibutyltin dilaurate if we wish to form a urethane bond between an hydroxyl-functionalized polymer and a functionalized isocyanate graft. The compound may finally be washed and dried, or even purified, according to the general knowledge of those skilled in the art.

According to another embodiment, the supramolecular polymer may be prepared according to a process comprising the following steps:

(i) Functionalization of the dihydroxylated polyalkene polymer P, previously dried, by a diisocyanate according to the reaction scheme:

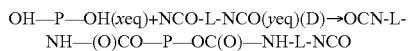

preferably in quantities such that the polyalkene polymer/diisocyanate D molar ratio (ratio x/y) ranges from 0.30 to 0.70, better still from 0.35 to 0.65, preferably from 0.4 to 0.6, more preferably from 0.45 to 0.55.

This first step may be made in the presence of solvent, at a temperature of between 20° C. and 100° C.

This first step may be followed by a period of stirring, in a controlled atmosphere for a period ranging from 1 hour to 24 hours. The mixture may optionally be heated.

The degree of progress of this first step may be monitored by assaying the hydroxyl functions;

then (ii) reaction of the pre-polymer obtained in step (i) with 6-methylisocytosine or 2-aminoethylimidazolidine:

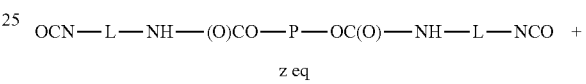

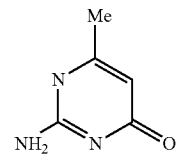

t eq or

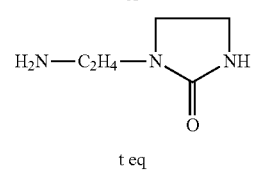

t eq preferably in a quantity such that the diisocyanate D/6-methylisocytosine or 2-aminoethylimidazolidine molar ratio (ratio y/t) ranges from 0.80 to 1.20.

This second step may optionally be performed in the presence of a cosolvent such as toluene, butyl acetate or propylene carbonate. The reaction mixture may be heated to between 80° C. and 140° C. for a time ranging between 1 and 24 hours.

The presence of a catalyst, such as for example dibutyltin dilaurate, may promote the production of the desired final product.

The reaction may be monitored by infrared spectroscopy, by monitoring the disappearance of the peak characteristic of isocyanate between 2200 and 2300 cm$^{-1}$.

At the end of the reaction, ethanol may be added to the reaction medium in order to neutralize any residual isocyanate functions. The reaction mixture may be optionally filtered. If necessary, the polymer may be directly stripped in a cosmetic solvent.

As polyalkene supramolecular polymer, those described in application FR-A-2938760 can be used, particularly the polymer of example 3.

Surfactant System of the Aqueous Dispersion:

The aqueous dispersion of polyalkene supramolecular polymer according to the invention also comprises a surfactant system that can maintain said polymer in dispersion in water stably for at least one week at ambient temperature (23° C.).

The surfactant system is chosen from:
1) A system containing at least one anionic surfactant optionally combined with at least one non-ionic surfactant, with the exclusion of the surfactant system containing only dodecyl sulfate and/or an alkali metal salt of dodecyl sulfate;
2) a system containing at least one cationic surfactant, optionally combined with at least one non-ionic surfactant;
3) a system containing at least one non-ionic surfactant having an HLB greater than 10 or a mixture of non-ionic surfactants, said mixture having an HLB greater than 10.
   According to a first embodiment of the invention, the surfactant system is one or more anionic surfactant(s).

This first embodiment excludes dodecyl sulfate and/or an alkali metal salt of dodecyl sulfate used as the only surfactant.

The term "anionic surfactant" means a surfactant comprising, as ionic or ionizable groups, only anionic groups.

In the present description, a species is termed "anionic" when it bears at least one permanent negative charge or when it can be ionized into a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

It is understood in the present description that:
the carboxylate anionic surfactants comprise at least one carboxylic or carboxylate function (—COOH or —COO$^-$) and may optionally also comprise one or more sulfate and/or sulfonate functions;
the sulfonate anionic surfactants comprise at least one sulfonate function (—SO$_3$H or —SO$_3^-$) and may optionally also comprise one or more sulfate functions, but do not comprise any carboxylate functions; and
the sulfate anionic surfactants comprise at least one sulfate function but do not comprise any carboxylate or sulfonate functions.

The carboxylic anionic surfactants therefore include at least one carboxylic or carboxylate function (—COOH or —COO$^-$).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds;
the alkyl and/or acyl groups of these compounds including from 6 to 30 carbon atoms, especially from 10 to 22, better still from 10 to 16 carbon atoms; said alkyl groups being linear or branched, where the aryl group preferably denotes a phenyl or benzyl group;
these compounds may be polyoxyalkylenated, especially polyoxyethylenated, and then preferably including from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

The salts of these compounds may be alkali metal (particularly sodium) or alkaline earth, ammonium, or aminoalcohol salts.

Preferably, the carboxylic anionic surfactants are chosen from acylsarcosinates or acylglycinates whose acyl group includes 10 to 22 carbon atoms and more particularly a linear acyl group including from 10 to 16 carbon atoms, particularly the sodium salt of N-lauroyl sarcosine and sodium N-cocoyl glycinate. Preferably, the acylsarcosinates cited previously are used and more particularly the sodium salt of N-lauroyl sarcosine.

The sulfonate anionic surfactants include at least one sulfonate function (—SO$_3$H or —SO$_3^-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;
the alkyl groups of these compounds comprising from 6 to 30 carbon atoms, in particular from 12 to 28, better still from 14 to 24 or even from 16 to 22 carbon atoms;
where the aryl group preferably denotes a phenyl or benzyl group;
where these compounds may be polyoxyalkylenated, in particular polyoxyethylenated, and then preferably comprising from 1 to 50 ethylene oxide units and better still from 2 to 25 ethylene oxide units, and preferably from 2 to 10.

The salts of these compounds may be alkali metal (particularly sodium) or alkaline earth, ammonium, or aminoalcohol salts.

The sulfate anionic surfactants that may be used comprise at least one sulfate function (—OSO$_3$H or —OSO$_3^-$).

They may be chosen from the following compounds: alkyl sulfates, alkyl ether sulfates, alkylamido ether sulfates, alkylaryl polyether sulfates, monoglyceride sulfates; and the salts of these compounds;
the alkyl groups of these compounds including from 6 to 30 carbon atoms, in particular from 12 to 28, better still from 14 to 24 or even from 16 to 22 carbon atoms; where the aryl group preferably denotes a phenyl or benzyl group;
these compounds may be polyoxyalkylenated, especially polyoxyethylenated, and then preferably including from 1 to 50 ethylene oxide units and better still from 2 to 25 ethylene oxide units, and preferably from 2 to 10.

The salts of these compounds may be alkali metal (particularly sodium) or alkaline earth, ammonium, or aminoalcohol salts.

Preferentially, the sulfate anionic surfactants are chosen from:
alkyl sulfates especially C6-C24, even C8-C20, such as dodecyl sulfate (not used as the only surfactant but always combined with a non-ionic surfactant) or decyl sulfate
alkyl ether sulfates, especially C6-C24, even C12-C22, preferably comprising from 2 to 25 ethylene oxide units, more preferably 2 to 10 ethylene oxide units, such as lauryl ether sulfate comprising from 2 to 25 ethylene oxide units
particularly in the form of alkali metal or alkaline earth metal, ammonium, or aminoalcohol salts, more particularly in the form of alkali metal salts such as sodium salts.

Preferably, the anionic surfactant is chosen from carboxylate surfactants and sulfate surfactants described previously.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline earth metal salts and in particular sodium or magnesium salts, preferably sodium, are preferably used.

The anionic surfactant is preferably chosen from sodium N-lauroyl sarcosinate, sodium laureth sulfate and sodium decyl sulfate.

The surfactant system may also comprise a non-ionic surfactant as described hereinafter in combination with the anionic surfactant as described previously.

Advantageously, the non-ionic surfactant combined may be chosen from: C8-C30 polyoxyethylenated fatty alcohols, especially C12-C18 fatty alcohols, particularly polyoxyethylenated lauryl, cetyl, myristyl, stearic alcohols having from 2 to 30 moles of ethylene oxide;
polyoxyethylenated C8-C30 fatty acid esters (preferably C12-C18) of sorbitan especially polyoxyethylenated esters of C12-C18 fatty acids, in particular lauric, myristic, cetylic or stearic acids, of sorbitan especially containing from 2 to 30 mol of ethylene oxide;
polyglycerolated C8-C30 fatty acid esters, especially polyglycerolated esters of C12-C18 fatty acids, in particular lauric, myristic, palmitic, stearic or isostearic acid, especially containing from 2 to 16 mol of glycerol.

The non-ionic surfactant combined is preferably chosen from:
4 EO or 23 EO (Laureth-23 or Laureth-4) polyoxyethylenated lauryl alcohols
polyoxyethylenated (20 EO) sorbitan monopalmitate
polyglyceryl-4 isostearate Surfactant System Advantageously, the anionic surfactant combined may be chosen from:
alkyl sulfates especially C6-C24, even C8-C20, such as dodecyl sulfate (not used as the only surfactant but always combined with a non-ionic surfactant) or decyl sulfate
acylsarcosinates whose acyl group includes 10 to 22 carbon atoms and more particularly a linear acyl group including from 10 to 16 carbon atoms, particularly the sodium salt of N-lauroyl sarcosine;
alkyl ether sulfates, especially C6-C24, even C12-C22, preferably comprising from 2 to 25 ethylene oxide units, more preferably 2 to 10 ethylene oxide units, such as lauryl ether sulfate comprising from 2 to 25 ethylene oxide units.

As combinations of anionic surfactant and non-ionic surfactant, mention may be made of:
polyoxyethylenated (20 EO) sorbitan monopalmitate/sodium decyl sulfate (especially according to 90/10 or 50/50 weight ratio)
polyoxyethylenated (20 EO) sorbitan monopalmitate/sodium N-lauroyl sarcosinate (especially 90/10)
Laurylethersulfate (2 EO)/polyoxyethylenated (20 EO) sorbitan monopalmitate (especially 10/90 or 50/50)
Laurylethersulfate (2 EO)/polyglyceryl-4 isostearate (especially 10/90)
Laurylethersulfate (2 EO)/polyglyceryl-4 isostearate (especially 50/50)

According to a second embodiment of the invention, the surfactant system contains one or more cationic surfactant(s).

The cationic surfactant is advantageously chosen from optionally polyoxyalkylenated primary, secondary or tertiary fatty amine salts, quaternary ammonium salts, and mixtures thereof.

As quaternary ammonium salts, mention may be made especially of:
quaternary ammonium salts having formula (Ia):

in which:
groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms, it being possible for the linear or branched aliphatic groups to include heteroatoms such as, especially, oxygen, nitrogen, sulfur, these heteroatoms not being adjacent, and halogens; and
$X^-$ is an anion chosen especially from the group of halides such as bromides, chlorides, iodides, fluorides, phosphates, acetates, lactates, ($C_1$-$C_4$)alkyl sulfates, ($C_1$-$C_4$) alkyl sulfonates or ($C_1$-$C_4$)alkylaryl sulfonates;
$C_1$-$C_{30}$ alkyl, $C_1$-$C_{30}$ alkoxy, ($C_2$-$C_6$)polyoxyalkylene, $C_1$-$C_{30}$ alkylamide, ($C_{12}$-$C_{22}$)alkyl-($C_2C_6$)alkylamido, ($C_{12}$-$C_{22}$)alkyl acetate and $C_1$-$C_{30}$ hydroxyalkyl groups;

Mention may be made especially of tetraalkylammonium halides, especially chlorides, such as dialkyldimethylammonium or alkyltrimethylammonium chlorides in which the alkyl group comprises from 12 to 22 carbon atoms, in particular from 14 to 20 carbon atoms such as behenyltrimethylammonium chloride, distearyldimethylammonium chloride, cetyltrimethylammonium chloride (or cetrimonium chloride) and benzyldimethylstearylammonium chloride.

Mention may also be made of palmitylamidopropyltrimethylammonium or stearamidopropyldimethyl-(myristyl acetate)-ammonium halides, and especially chlorides, especially the product sold under the name Ceraphyl® 70 by the company Van Dyk.

Preferably, cationic surfactants having formula (Ia) are chosen from alkyltrimethylammonium halides whose alkyl group includes from 12 to 22 carbon atoms, more preferably from 14 to 20 carbon atoms and more particularly alkyltrimethylammonium chlorides such as behenyltrimethylammonium chloride and cetyltrimethylammonium chloride.

quaternary ammonium salts of imidazoline having formula (IIa):

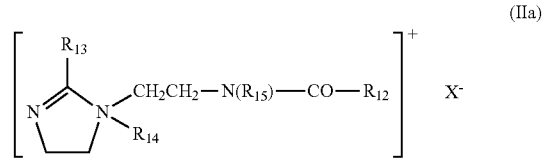

wherein

R$_{12}$ represents an alkenyl or alkyl group comprising from 8 to 30 carbon atoms, for example derived from tallow fatty acids, R$_{13}$ represents a hydrogen atom, a C$_1$-C$_4$ alkyl group or an alkenyl or alkyl group comprising from 8 to 30 carbon atoms, R$_{14}$ represents a C$_1$-C$_4$ alkyl group, R$_{15}$ represents a hydrogen atom or a C$_1$-C$_4$ alkyl group, X$^-$ is an anion chosen especially from the group of halides, phosphates, acetates, lactates, (C$_1$-C$_4$)alkyl sulfates, and (C$_1$-C$_4$)alkyl- or (C$_1$-C$_4$)alkylarylsulfonates;

Preferably, R$_{12}$ and R$_{13}$ denote a mixture of alkenyl or alkyl groups comprising from 12 to 21 carbon atoms, for example derived from tallow fatty acids, R$_{14}$ denotes a methyl group and R$_{15}$ denotes a hydrogen atom. Such a product is sold, for example, under the name Rewoquat® W75 or W90 by the company Evonik.

di- or triquaternary ammonium salts having formula (IIIa):

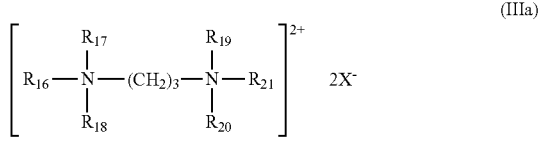

(IIIa)

in which:

R$_{16}$ denotes an alkyl group comprising from 16 to 30 carbon atoms, which is optionally hydroxylated and/or optionally interrupted with one or more oxygen atoms, R$_{17}$ denotes hydrogen, an alkyl group comprising from 1 to 4 carbon atoms or a group —(CH$_2$)$_3$—N$^+$(R$_{16a}$)(R$_{17a}$)(R$_{18a}$), R$_{16a}$, R$_{17a}$ and R$_{18a}$, which may be identical or different, denoting hydrogen or an alkyl group comprising from 1 to 4 carbon atoms, R$_{18}$, R$_{19}$, R$_{20}$ and R$_{21}$, which may be identical or different, denote hydrogen or an alkyl group comprising from 1 to 4 carbon atoms, and X$^-$ is an anion, chosen especially from the group of halides, acetates, phosphates, nitrates, (C$_1$-C$_4$)alkyl sulfates and (C$_1$-C$_4$)alkyl- and (C$_1$-C$_4$)alkylarylsulfonates, in particular methyl sulfate and ethyl sulfate;

Such compounds are, for example, Finquat CT-P (Quaternium 89) and Finquat CT (Quaternium 75), sold by the company Finetex.

quaternary ammonium salts containing one or more ester functions, having formula (IVa) below:

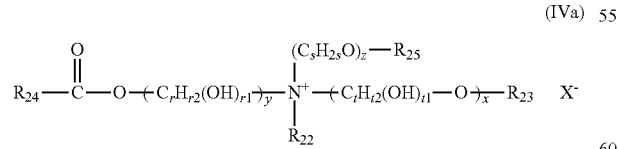

(IVa)

in which:

R$_{22}$ is chosen from C$_1$-C$_6$ alkyl groups and C$_1$-C$_6$ hydroxyalkyl or dihydroxyalkyl groups, R$_{23}$ is chosen from the group R$_{26}$—C(=O)—; linear or branched, saturated or unsaturated C$_1$-C$_{22}$ hydrocarbon-based groups R$_{27}$; and a hydrogen atom, R$_{25}$ is chosen from the group R$_{28}$—C(=O)—; linear or branched, saturated or unsaturated C$_1$-C$_6$ hydrocarbon-based groups R$_{29}$; and a hydrogen atom, R$_{24}$, R$_{26}$ and R$_{28}$, which may be identical or different, are chosen from saturated or unsaturated, linear or branched C$_7$-C$_{21}$ hydrocarbon-based groups, r, s and t, which may be identical or different, are integers ranging from 2 to 6, r1 and t1, which may be identical or different, are equal to 0 or 1, y is an integer ranging from 1 to 10, x and z, which may be identical or different, are integers ranging from 0 to 10, X$^-$ is an anion, it being understood that r2+r1=2r and t1+t2=2t, and that the sum x+y+z ranges from 1 to 15, with the proviso that when x=0 then R$_{23}$ denotes R$_{27}$ and that when z=0 then R$_{25}$ denotes R$_{29}$.

The alkyl groups R$_{22}$ may be linear or branched, preferably linear. Preferably, R$_{22}$ denotes a methyl, ethyl, hydroxyethyl or dihydroxypropyl group, and more particularly a methyl or ethyl group.

Advantageously, the sum x+y+z ranges from 1 to 10.

When R$_{23}$ is a hydrocarbon-based group R$_{27}$, it may comprise from 12 to 22 carbon atoms, or else may comprise from 1 to 3 carbon atoms.

When R$_{25}$ is a hydrocarbon-based group R$_{29}$, it preferably contains 1 to 3 carbon atoms.

Advantageously, R$_{24}$, R$_{26}$ and R$_{28}$, which may be identical or different, are chosen from linear or branched, saturated or unsaturated C$_{11}$-C$_{21}$ hydrocarbon-based groups, and more particularly from linear or branched C$_{11}$-C$_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion X$^-$ is preferably a halide, preferably chloride, bromide or iodide, a (C$_1$-C$_4$)alkyl sulfate, a (C$_1$-C$_4$)alkylsulfonate or a (C$_1$-C$_4$)alkylarylsulfonate, a methanesulfonate, a phosphate, a nitrate, a tosylate, an anion derived from an organic acid such as an acetate or a lactate or any other anion that is compatible with the ammonium bearing an ester function. The anion X$^-$ is more particularly a chloride, a methyl sulfate or an ethyl sulfate.

Use is made more particularly of the ammonium salts having formula (VII) in which:

R$_{22}$ denotes a methyl or ethyl group, x and y are equal to 1, z is equal to 0 or 1, r, s and t are equal to 2, R$_{23}$ is chosen from the group R$_{26}$—C(=O)—, methyl, ethyl or C$_{14}$-C$_{22}$ hydrocarbon-based groups; and a hydrogen atom, R$_{25}$ is chosen from the group R$_{28}$—C(=O)—; and a hydrogen atom, R$_{24}$, R$_{26}$ and R$_{28}$, which may be identical or different, are chosen from linear or branched, saturated or unsaturated C$_{13}$-C$_{17}$ hydrocarbon-based groups, and preferably from linear or branched, saturated or unsaturated C$_{13}$-C$_{17}$ alkyl and alkenyl groups.

Advantageously, the hydrocarbon-based groups are linear.

Among the compounds having formula (IVa), mention may be made of salts, especially the chloride or methyl sulfate of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures especially of plant or animal origin, or by transesterification of the methyl esters thereof. This esterification may be followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are sold, for example, under the names Dehyquart® by the company Henkel, Stepanquat® by the company Stepan, Noxamium® by the company CECA or Rewoquat® WE 18 by the company Evonik.

The mixture of cationic surfactants may contain, for example, a mixture of quaternary ammonium monoester, diester and triester salts with a weight majority of diester salts. Use may also be made of the ammonium salts containing at least one ester functional group that are described in patents U.S. Pat. Nos. 4,874,554 and 4,137,180. Use may also be made of behenoylhydroxypropyl-trimethylammonium chloride, for example, sold by the company Kao under the name Quartamin BTC 131.

Preferably, the ammonium salts containing at least one ester function contain two ester functions.

More preferably, cationic surfactants used according to the invention are chosen from those having formula (Ia), among alkyltrimethylammonium salts whose alkyl group includes from 12 to 22 carbon atoms, more preferably from 14 to 20 carbon atoms and more particularly behenyltrimethylammonium salts, cetrimonium slats and particularly cetyltrimethylammonium chloride, behenyltrimethylammonium chloride or their mixtures.

The surfactant system may also comprise a non-ionic surfactant as described hereinafter in combination with the cationic surfactant as described previously. The non-ionic surfactant is preferably chosen from:
polyoxyethylenated lauryl alcohol 4 EO (Laureth-4), polyoxyethylenated lauryl alcohol 23 EO (Laureth-23), polyoxyethylenated (20 EO) sorbitan monopalmitate polyglyceryl-4 isostearate.

As combinations of cationic surfactant and non-ionic surfactant, mention may be made of:
cetrimonium chloride/polyoxyethylenated sorbitan monopalmitate (20 EO) (especially 10/90)
behenyltrimethylammonium chloride/polyoxyethylenated sorbitan monopalmitate (20 EO) (especially 10/90)
cetrimonium chloride/polyglyceryl-4 isostearate (especially 10/90) behenyl trimethylammonium chloride/polyglyceryl-4 isostearate (especially 10/90)

According to a third embodiment of the invention, the surfactant system contains one or more non-ionic surfactants.

The non-ionic surfactant may be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms and especially from 16 to 30 carbon atoms;

Mention may also be made of polyethoxylated fatty amides preferably having from 2 to 30 ethylene oxide units, polyglycerolated fatty amides including on average from 1 to 5, and in particular from 1.5 to 4, glycerol groups; polyoxyethylenated fatty acid esters of sorbitan having preferably from 2 to 40 units of ethylene oxide, fatty acid esters of sucrose, polyoxyalkylenated and preferably polyoxyethylenated fatty acid esters containing from 2 to 150 mol of ethylene oxide, such as oxyethylenated plant oils.

Mention may also be made of non-ionic surfactants of alkyl(poly)glycoside type, represented especially by the following general formula: $R_1O—(R_2O)_t-(G)_v$ in which:

$R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms;

$R_2$ represents an alkylene substituent comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkyl(poly)glycoside surfactants are compounds of the formula described above in which:

$R_1$ denotes a linear or branched, saturated or unsaturated alkyl substituent comprising from 8 to 18 carbon atoms, $R_2$ represents an alkylene substituent comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$ alkyl(poly)glucosides 1,4, and in particular decyl glucosides and caprylyl/capryl glucosides, are most particularly preferred.

Among commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of $C_8/C_{16}$-alkyl (poly)glycosides 1,4, in particular as an aqueous 53% solution, such as those sold by Cognis under the reference Plantacare® 818 UP.

Preferably, the non-ionic surfactants are chosen from polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol;
and mixtures thereof.

The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as:
cetyl alcohol polyoxyethylenated with 2 EO (Ceteth-2) (HLB 5.3)
cetyl alcohol polyoxyethylenated with 6 EO (Ceteth-6) (HLB 11.1)
cetyl alcohol polyoxyethylenated with 10 EO (Ceteth-10) (HLB 12.9)
cetyl alcohol polyoxyethylenated with 20 EO (Ceteth-20) (HLB 15.7)
cetyl alcohol polyoxyethylenated with 24 EO (Ceteth-24) (HLB 16.3)
lauryl alcohol polyoxyethylenated with 2 EO (Laureth-2) (HLB 6.1)
lauryl alcohol polyoxyethylenated with 3 EO (Laureth-3) (HLB 8)
lauryl alcohol polyoxyethylenated with 4 EO (Laureth-4) (HLB 9.4)
lauryl alcohol polyoxyethylenated with 7 EO (Laureth-7) (HLB 12.3)
lauryl alcohol polyoxyethylenated with 9 EO (Laureth-9) (HLB 13.6)
lauryl alcohol polyoxyethylenated with 10 EO (Laureth-10) (HLB 13.9)
lauryl alcohol polyoxyethylenated with 12 EO (Laureth-12) (HLB 14.6)
lauryl alcohol polyoxyethylenated with 21 EO (Laureth-21) (HLB 15.5) lauryl alcohol polyoxyethylenated with 23 EO (Laureth-23) (HLB 16.3)
stearyl alcohol polyoxyethylenated with 2 EO (Steareth-2) (HLB 4.9)
stearyl alcohol polyoxyethylenated with 10 EO (Steareth-10) (HLB 12.4)
stearyl alcohol polyoxyethylenated with 20 EO (Steareth-20) (HLB 15.2)
stearyl alcohol polyoxyethylenated with 21 EO (Steareth-21) (HLB 15.5)

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as:
polyoxyethylenated sorbitan monolaurate (4 EO) (Polysorbate-21) (HLB 13.3)
polyoxyethylenated sorbitan monolaurate (20 EO) (Polysorbate-20) (HLB 16.7)
polyoxyethylenated sorbitan monopalmitate (20 EO) (Polysorbate-40) (HLB 15.6)
polyoxyethylenated sorbitan monostearate (20 EO) (Polysorbate-60) (HLB 14.9)
polyoxyethylenated sorbitan monostearate (4 EO) (Polysorbate-61) (HLB 9.6)
polyoxyethylenated sorbitan monooleate (20 EO) (Polysorbate-80) (HLB 15)

The polyglycerolated C8-C30 fatty acid esters may be chosen from polyglycerolated esters of C12-C18 fatty acids, in particular lauric, myristic, palmitic, stearic or isostearic acid, having from 2 to 16 mol of glycerol, such as:
polyglyceryl-2 laurate, polyglyceryl-3 laurate, polyglyceryl-4 laurate, polyglyceryl-5 laurate, polyglyceryl-6 laurate, polyglyceryl-10 laurate;
polyglyceryl-2 myristate, polyglyceryl-3 myristate, polyglyceryl-4 myristate, polyglyceryl-5 myristate, polyglyceryl-6 myristate, polyglyceryl-10 myristate;
polyglyceryl-2 palmitate, polyglyceryl-3 palmitate, polyglyceryl-6 palmitate, polyglyceryl-10 palmitate;
polyglyceryl-2 isostearate, polyglyceryl-3 isostearate, polyglyceryl-4 isostearate,
polyglyceryl-5 isostearate, polyglyceryl-6 isostearate, polyglyceryl-10 isostearate;
polyglyceryl-2 stearate, polyglyceryl-3 stearate, polyglyceryl-4 stearate,
polyglyceryl-5 stearate, polyglyceryl-6 stearate, polyglyceryl-8 stearate,
polyglyceryl-10 stearate.

The non-ionic surfactant is preferably chosen from polyoxyethylenated lauryl alcohol (4 EO), polyoxyethylenated lauryl alcohol (23 EO), oxyethylene sorbitan monopalmitate (20 EO), polyglyceryl-4 isostearate.

When the surfactant system comprises a non-ionic surfactant and an anionic or cationic surfactant, said non-ionic surfactant may have any HLB at all.

When the surfactant system comprises only a non-ionic surfactant, the surfactant then has an HLB greater than 10, and preferably greater than or equal to 15.

When the surfactant system comprises only a mixture of non-ionic surfactants, said mixture then has an HLB greater than 10, and preferably greater than or equal to 15.

The term HLB is well known to those skilled in the art, and denotes the hydrophilic-lipophilic balance of a surfactant at 25° C. in the Griffin sense.

The term "hydrophilic-lipophilic balance (HLB)" is intended to mean the equilibrium between the size and the strength of the hydrophilic group and the size and the strength of the lipophilic group of the surfactant. This HLB value according to Griffin is defined in J. Soc. Cosm. Chem. 1954 (volume 5), pages 249-256.

Surfactants having an HLB greater than 10 can be used that are cited in the reference work *McCutcheons Emulsifiers & Detergents*, International Edition, 1998 and following.

Reference may also be made to Kirk-Othmer's Encyclopedia of Chemical Technology, volume 22, pp. 333-432, 3rd edition, 1979, Wiley, for the definition of the emulsifying properties and functions of surfactants, in particular pp. 347-377 of this reference, for non-ionic surfactants.

The HLB of a surfactant mixture containing a % of A and b % of B (mass percentage) is calculated as follows:

$$HLB(A+B) = a\% \, (HLB\ A) + b\% \, (HLB\ B)$$

As an example of non-ionic surfactants with HLB greater than 10, the surfactants described previously can be used, and preferably chosen from oxyethylene sorbitan monopalmitate (20 EO) (HLB=15.3), Laureth-23 (HLB=16.3) and Laureth-9 (13.6), As examples of non-ionic surfactants with HLB less than or equal to 10, mention may be made for example of polyglyceryl-4 isostearate (HLB=5), Laureth-4 (HLB=9.4), Laureth-2 (HLB=6.1) and Laureth-3 (HLB=8).

As non-ionic surfactant mixture, mention may be made of the mixture of polyoxyethylenated lauryl alcohol 4 EO and polyoxyethylenated lauryl alcohol 23 EO.

The polyalkene supramolecular polymer may be present in the aqueous dispersion in a content ranging from 2% to 50% by weight and preferably ranging from 5% to 40% by weight, relative to the total weight of the dispersion.

The surfactant system may be present in the aqueous composition in a content ranging from 0.01% to 5% by weight, especially ranging from 0.02% to 4% by weight, preferably ranging from 0.03% to 3% by weight, more preferably ranging from 0.04% to 2% by weight, relative to the total weight of the dispersion.

Advantageously, the polyalkene supramolecular polymer and the surfactant system are present in the aqueous dispersion according to a polymer/surfactant weight ratio ranging from 9 to 49, preferably ranging from 9 to 40, preferably ranging from 9 to 35.

A subject of the invention is also a process for preparing the aqueous dispersion described previously, comprising the following steps:
(i) a synthesis step of the polyalkene supramolecular polymer in an organic solvent S like for example the 2-methyl tetrahydrofuran, ethyl acetate;
(ii) then an addition step:
either of an aqueous solution containing the surfactant system,
or of an organic solution containing the organic solvent S and the surfactant system then water addition;
(iii) then a step of dispersion of the mixture obtained under stirring, especially at a rate ranging from 3000 to 30000 rpm, especially for a duration ranging from 1 to 60 minutes preferably ranging from 5 to 15 minutes;
(iv) then a step of evaporation of the organic solvent S.

The step of dispersion may be conducted with stirring using a disperser, for example with a rotor/stator such as an Ultra Turax, for example at the rate of 24,000 rpm.

The invention also relates to a composition comprising the aqueous dispersion of the polyalkene supramolecular polymer described previously.

The supramolecular polymer may be present in the composition according to the invention in a content ranging from 0.1% to 50% by weight, preferably ranging from 0.5% to 40% by weight, more preferably ranging from 0.5% to 30% by weight, relative to the total weight of the composition.

Pigments

The composition of use in the process of the invention comprises at least one pigment. The term "pigment" is intended to mean all pigments which give keratin materials colour. Their solubility in water at 25° C. and at atmospheric pressure (760 mmHg) is less than 0.05% by weight, and preferably less than 0.01%.

The pigments which can be used are in particular chosen from organic and/or mineral pigments known in the art, in particular those which are described in the Kirk-Othmer encyclopaedia of chemical technology and in the Ullmann encyclopaedia of industrial chemistry.

These pigments can be in the form of a pigment powder or paste. They can be coated or uncoated.

The pigments can for example be chosen from mineral pigments, organic pigments, lakes, special-effect pigments such as nacres or glitter flakes, and mixtures thereof. The pigment may be a mineral pigment. The term "mineral pigment" is intended to mean any pigment which satisfies the definition of the Ullmann encyclopaedia in the chapter on inorganic pigments. Among the mineral pigments used in the present invention, mention may be made of iron or chromium oxides, manganese violet, ultramarine blue, chromium hydrate, ferric blue and titanium oxide.

The pigment may be an organic pigment. The term "organic pigment" is intended to mean any pigment which satisfies the definition of the Ullmann encyclopaedia in the chapter on organic pigments. The organic pigment may in particular be chosen from nitroso, nitro, azo, xanthene, quinoline, anthraquinone, phthalocyanine, metal complex, isoindolinone, isoindoline, quinacridone, perinone, perylene, diketopyrrolopyrrole, thioindigo, dioxazine, triphenylmethane and quinophthalone compounds.

In particular, the white or coloured organic pigments can be chosen from carmine lake, carbon black, aniline black, azo yellow, quinacridone, phthalocyanine blue, sorghum red, the blue pigments codified by the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in Patent FR 2 679 771.

The pigments in accordance with the invention can also be in the form of composite pigments as described in Patent EP 1 184 426. These composite pigments can be composed in particular of particles comprising an inorganic core, at least one binder ensuring the binding of the organic pigments to the core, and at least one organic pigment which at least partially covers the core.

The organic pigment can also be a lake. The term "lake" is intended to mean the dyes adsorbed onto insoluble particles, the assembly thus obtained remaining insoluble during use.

The inorganic substrates onto which the dyes are adsorbed are, for example, alumina, silica, calcium sodium borosilicate, calcium aluminium borosilicate, and aluminium.

Among the dyes, mention may be made of carmine cochineal. Mention may also be made of the dyes known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 0 (CI 77 002), D & C Green 3 (CI 42 053) or D & C Blue 1 (CI 42 090).

By way of examples of lakes, mention may be made of the product sold under the following name: D & C Red 7 (0115 850:1).

The pigment can also be a special-effect pigment. The term "special-effect pigments" is intended to mean pigments which generally create a coloured appearance (characterized by a certain shade, a certain vivacity and a certain level of luminance) which is non-uniform and which changes as a function of the conditions of observation (light, temperature, angles of observation, etc.). They thereby contrast with coloured pigments that provide a conventional uniform opaque, semi-transparent or transparent tint.

There are several types of special-effect pigments, those with a low refractive index, such as fluorescent, photochromic or thermochromic pigments, and those with a higher refractive index, such as nacres or glitter flakes.

By way of examples of special-effect pigments, mention may be made of nacreous pigments such as titanium mica coated with an iron oxide, mica coated with iron oxide, mica coated with bismuth oxychloride, titanium mica coated with chromium oxide, titanium mica coated with an organic dye, in particular of the abovementioned type, and also nacreous pigments based on bismuth oxychloride. It may also involve particles of mica at the surface of which are superimposed at least two successive layers of metal oxides and/or of organic colorants.

The nacres may more particularly have a yellow, pink, red, bronze, orangey, brown, gold and/or coppery colour or glint.

By way of illustration of the nacres that can be used in the context of the present invention, mention may in particular be made of the gold-coloured nacres sold in particular by the company Engelhard under the name Gold 222C (Cloisonne), Sparkle gold (Timica), Gold 4504 (Chromalite) and Monarch gold 233X (Cloisonne); the bronze nacres sold in particular by the company MERCK under the name Bronze fine (17384) (Colorona) and Bronze (17353) (Colorona), by the company Eckart under the name Prestige Bronze and by the company Engelhard under the name Super bronze (Cloisonne); the orange nacres sold in particular by the company Engelhard under the name Orange 363C (Cloisonne) and Orange MCR 101 (Cosmica) and by the company MERCK under the name Passion orange (Colorona) and Matte orange (17449) (Microna); the brown-tinted nacres sold in particular by the company Engelhard under the name Nu-antique copper 340XB (Cloisonne) and Brown CL4509 (Chromalite); the nacres with a copper glint sold in particular by the company Engelhard under the name Copper 340A (Timica) and by the company Eckart under the name Prestige Copper; the nacres with a red glint sold in particular by the company Merck under the name Sienna fine (17386) (Colorona); the nacres with a yellow glint sold in particular by the company Engelhard under the name Yellow (4502) (Chromalite); the red-tinted nacres with a gold glint sold in particular by the company Engelhard under the name Sunstone G012 (Gemtone); the black nacres with a gold tint sold in particular by the company Engelhard under the name Nu antique bronze 240 AB (Timica), the blue nacres sold in particular by the company Merck under the name Matte blue (17433) (Microna), Dark Blue (117324) (Colorona), the white nacres with a silvery glint sold in particular by the company Merck under the name Xirona Silver and the golden-green-pink-orange nacres sold in particular by the company Merck under the name Indian summer (Xirona) and mixtures thereof.

In addition to the nacres on a mica support, it is possible to envisage multilayer pigments based on synthetic substrates such as alumina, silica, calcium sodium silicate, calcium aluminium borosilicate, and aluminium.

Mention may also be made of the pigments with an interference effect not bound to a substrate, for instance liquid crystals (Helicones HC from Wacker), holographic interference flakes (Geometric Pigments or Spectra f/x from Spectratek). The special-effect pigments also comprise fluorescent pigments, whether they are substances which are fluorescent in daylight or substances which produce an ultraviolet fluorescence, phosphorescent pigments, photochromic pigments, thermochromic pigments and quantum dots, sold for example by the company Quantum Dots Corporation.

The variety of pigments which can be used in the present invention makes it possible to obtain a rich pallet of colours, and also specific optical effects, such as interference, metallic effects.

The size of the pigment used in the cosmetic composition according to the present invention is generally between 10 nm and 200 µm, preferably between 20 nm and 80 µm, and more preferably between 30 nm and 50 µm.

The pigments may be dispersed in the product by virtue of a dispersing agent.

The dispersing agent serves to protect the dispersed particles against agglomeration or flocculation thereof. This dispersing agent may be a surfactant, an oligomer, a polymer or a mixture of several of them, bearing one or more functionalities having a strong affinity for the surface of the particles to be dispersed. In particular, they can physically or chemically attach to the surface of the pigments. These dispersants also have at least one functional group which is compatible or soluble in the continuous medium. In particular, use is made of esters of 12-hydroxystearic acid, in particular and of $C_8$ to $C_{20}$ fatty acid and of polyol, for instance glycerol or diglycerol, such as the stearate of poly(12-hydroxystearic acid) with a molecular weight of approximately 750 g/mol, such as that sold under the name Solsperse 21 000 by the company Avecia, polyglyceryl-2 dipolyhydroxy-stearate (CTFA name) sold under the reference Dehymyls PGPH by the company Henkel or else polyhydroxystearic acid such as that sold under the reference Arlacel P100 by the company Uniqema, and mixtures thereof.

As other dispersant that can be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention can be surface-treated with an organic agent.

Thus, the pigments surface-treated beforehand that are of use in the context of the invention are pigments which have been completely or partially subjected to a surface treatment of chemical, electronic, electrochemical, mechanochemical or mechanical nature with an organic agent such as those which are described in particular in Cosmetics and Toiletries, February 1990, Vol. 105, p. 53-64, before being dispersed in the composition in accordance with the invention. These organic agents can for example be chosen from amino acids; waxes, for example carnauba wax and beeswax; fatty acids; fatty alcohols and derivatives thereof, such as stearic acid, hydroxystearic acid, stearyl alcohol, hydroxystearyl alcohol, lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example poly(methyl methacrylate)s; polymers and copolymers containing acrylate units; proteins; alkanolamines; silicone compounds, for example silicones, polydimethylsiloxanes, alkoxysilanes, alkylsilanes and siloxy silicates; fluorinated organic compounds, for example perfluoroalkyl ethers; fluorosilicone compounds.

The surface-treated pigments that are of use in the cosmetic composition according to the invention may also have been treated with a mixture of these compounds and/or have been subjected to several surface treatments.

The surface-treated pigments that are of use in the context of the present invention can be prepared according to surface treatment techniques well known to those skilled in the art, or may be commercially available in the required form.

Preferably, the surface-treated pigments are coated with an organic layer.

The organic agent with which the pigments are treated can be deposited on the pigments by solvent evaporation, chemical reaction between the molecules of the surface agent or creation of a covalent bond between the surface agent and the pigments.

The surface treatment can thus be carried out for example by chemical reaction of a surface agent with the surface of the pigments and creation of a covalent bond between the surface agent and the pigments or the fillers. This method is in particular described in U.S. Pat. No. 4,578,266.

Preferably, an organic agent covalently bonded to the pigments will be used.

The agent for the surface treatment can represent from 0.1% to 50% by weight of the total weight of the surface-treated pigments, preferably from 0.5% to 30% by weight, and even more preferably from 1% to 10% by weight.

Preferably, the surface treatments of the pigments are chosen from the following treatments:
  a PEG-silicone treatment, for instance the AQ surface treatment sold by LCW;
  a chitosan treatment, for instance the CTS surface treatment sold by LCW;
  a triethoxycaprylylsilane treatment, for instance the AS surface treatment sold by LCW;
  a methicone treatment, for instance the SI surface treatment sold by LCW;
  a dimethicone treatment, for instance the Covasil 3.05 surface treatment sold by LCW;
  a dimethicone/trimethyl siloxysilicate treatment, for instance the Covasil 4.05 surface treatment sold by LCW;
  a lauroyl lysine treatment, for instance the LL surface treatment sold by LCW;
  a lauroyl lysine dimethicone treatment, for instance the LL/SI surface treatment sold by LCW;
  a magnesium myristate treatment, for instance the MM surface treatment sold by LCW;
  an aluminium dimyristate treatment, for instance the MI surface treatment sold by Miyoshi;
  a perfluoropolymethylisopropyl ether treatment, for instance the FHC surface treatment sold by LCW;
  an isostearyl sebacate treatment, for instance the HS surface treatment sold by Miyoshi;
  a disodium stearoyl glutamate treatment, for instance the NAI surface treatment sold by Miyoshi;
  a dimethicone/disodium stearoyl glutamate treatment, for instance the SA/NAI surface treatment sold by Miyoshi;
  a perfluoroalkyl phosphate treatment, for instance the PF surface treatment sold by Daito;
  an acrylate/dimethicone copolymer and perfluoroalkyl phosphate treatment, for instance the FSA surface treatment sold by Daito;
  a polymethylhydrogenosiloxane/perfluoroalkyl phosphate treatment, for instance the FS01 surface treatment sold by Daito;
  a lauryl lysine/aluminium tristearate treatment, for instance the LL-StAl surface treatment sold by Daito;
  an octyltriethylsilane treatment, for instance the OTS surface treatment sold by Daito;
  an octyltriethylsilane/perfluoroalkyl phosphate treatment, for instance the FOTS surface treatment sold by Daito;
  an acrylate/dimethicone copolymer treatment, for instance the ASC surface treatment sold by Daito;
  an isopropyl titanium triisostearate treatment, for instance the ITT surface treatment sold by Daito;
  a microcrystalline cellulose and carboxymethylcellulose treatment, for instance the AC surface treatment sold by Daito;
  a cellulose treatment, for instance the C2 surface treatment sold by Daito;
  an acrylate copolymer treatment, for instance the APD surface treatment sold by Daito;
  a perfluoroalkyl phosphate/isopropyl titanium triisostearate treatment, for instance the PF+ITT surface treatment sold by Daito.

The composition in accordance with the present invention can additionally comprise one or more non-surface-treated pigments.

According to one particular embodiment of the invention, the pigment(s) are mineral pigments.

According to another particular embodiment of the invention, the pigment(s) are chosen from nacres.

The amount of pigments can range from 0.5% up to 40%, and preferably from 1 to 20%.

The composition according to the invention may comprise at least one cosmetic ingredient chosen from colorants, fillers, oils, waxes, pastes, (additional) surfactants, UV filters, cosmetic actives; fragrances, propellants, film-forming polymers (additional, especially different from the polymer of the aqueous dispersion), thickeners, preservatives.

The invention is illustrated in greater detail in the following examples.

Polymer 1:
  described in example 2 of FR-A-2938760
  106.1 g of dihydroxylated hydrogenated 1,2-polybutadiene polymer (GI2000 from Nisso, Mn=2100) is heated in the presence of 22 mg of catalyst (dibutyltin dilaurate) at 80° C., under reduced pressure, for two hours. The temperature of the mixture is reduced to 20° C., under argon, followed by addition of 10 ml of isododecane and 19.3 g of isophorone diisocyanate (IPDI). The mixture is stirred for 16 hours at 20° C. under a controlled atmosphere, and is then heated to 120° C., followed by addition of 25 ml of propylene carbonate. 12 g of 6-methylisocytosine is added, resulting in a homogeneous white suspension. This suspension is heated to 140° C. and stirred at this temperature for 6 hours. The reaction is monitored by infrared spectroscopy, up to the total disappearance of the characteristic peak for isocyanates (2250 cm$^{-1}$). The mixture is then reduced to 30° C., and 400 ml of heptane, 200 ml of THF and 50 ml of ethanol are added, followed by filtration through Celite. The mixture is then stripped with isododecane.

A solution of the polymer in isododecane, with a solids content of 20%, is finally obtained; the polymer is characterized by GPC (Mn=7000 and polydispersity index=2.05).

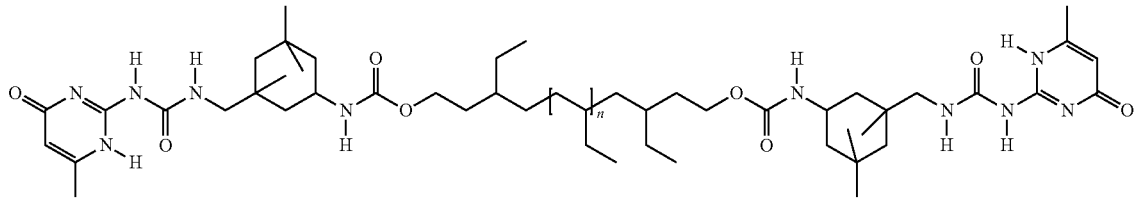

Polymer P2: Synthesis

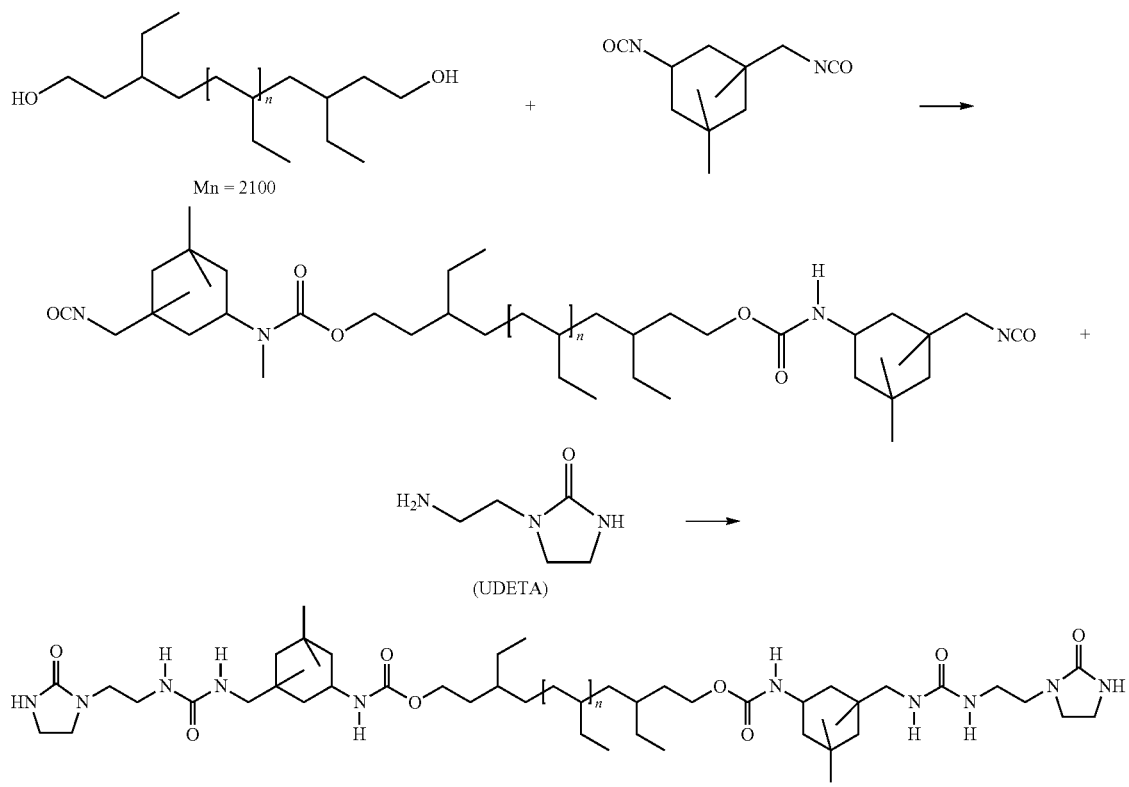

To a reactor under an argon atmosphere, 200 g of dihydroxylated hydrogenated 1,2-polybutadiene polymer (GI 2000 from Nisso; Mn=2100), 50 g of isododecane and 36.1 g of isophorone diisocyanate were added. The solution was heated to 40° C., then 63 μl of catalyst (dibutyltin dilaurate) was added, holding the temperature between 38° C. and 42° C. for three hours. Next 19.25 g of 2-aminoethylimidazolidin-2-one (UDETA) was added and the medium was heated to 120° C. for three hours. Then the temperature in the reactor was lowered to 70° C. and 100 ml of ethanol was added. The mixture was left to react for 1 hour. 350 g of isododecane was added and the ethanol was removed by distillation. A solution containing 38.5% by weight of polymer in isododecane was thus obtained.

The polymer obtained has a number-average molecular weight (Mn) of 4600 and a weight-average molecular weight (Mw) of 10400. (analysis by GPC)

Polymer 3:

The polymer P3 was obtained from the synthesis disclosed for Polymer 1 but the resulting solution of polymer P3 in isododecane, has a solids content of 20%, and; the polymer is characterized by GPC and has Mn=4200 and polydispersity index=2.24.

Examples of Aqueous Polymer Dispersions:

Example of Dispersion 1:

To a jacketed reactor set at the temperature of 15° C., 50 g of solution of polymer 1 at 10% by weight in 2-methyl tetrahydrofuran (2-Me THF) was added. Then with stirring using an Ultra-Turax at 24000 rpm for 10 min, an aqueous solution made by mixing 0.4 g of sodium lauryl ether sulfate (2 EO) and 50 g of water was added. The white solution obtained was then evaporated under vacuum to remove the 2 Me-THF.

Accordingly, we obtained an aqueous dispersion of Polymer 1 which is homogeneous, white and stable after one week's storage and one month's storage at ambient temperature (23° C.). This dispersion has solids content of 18%.

Other aqueous dispersions of Polymer 1, Polymer 2 and Polymer 3 with other surfactants described in Table 1 hereinafter according to the procedure described previously were prepared (surfactant content for sodium N-lauroyl sarcosinate of 2.8 g). To use the surfactant, it can be put in solution in 50 g of 2-Me THF in the place of water as specified in the table, then 50 g of water is added.

For each aqueous dispersion prepared, the stability was evaluated after one month's storage at ambient temperature (23° C.)

Examples 1 to 11: Aqueous Dispersions with Anionic Surfactant System

| Example | Polymer | Surfactant system (in water) | Polymer/ surfactant ratio | Solids content of the dispersion |
|---|---|---|---|---|
| 1 | Polymer 1 | Sodium N-lauroyl sarcosinate (water) | 97/3 | 20.4% |
| 2 | Polymer 1 | Sodium lauryl ether sulfate 2 EO (water) | 91/9 | 18% |
| 3 | Polymer 1 | Sodium lauryl ether sulfate 2 EO (water)/ polyoxyethylenated sorbitan monopalmitate (20 EO) (2-MeTHF) 50/50 | 91/9 | 25% |

-continued

| Example | Polymer | Surfactant system (in water) | Polymer/ surfactant ratio | Solids content of the dispersion |
|---|---|---|---|---|
| 4 | Polymer 1 | Sodium lauryl ether sulfate 2 EO (water)/ polyoxyethylenated sorbitan monopalmitate (20 EO) (2-Me—THF) 10/90 | 91/9 | 20% |
| 5 | Polymer 1 | Sodium lauryl ether sulfate 2 EO (water)/ polyglyceryl-4 isostearate (2 Me—THF) 50/50 | 91/9 | 15% |
| 6 | Polymer 1 | Mixture of polyoxyethylenated sorbitan monopalmitate (20 EO)/sodium dodecyl sulfate (90/10) | 91/9 | 11% |
| 7 | Polymer 1 | Mixture of polyoxyethylenated sorbitan monopalmitate (20 EO)/sodium dodecyl sulfate (50/50) | 91/9 | 13% |
| 8 | Polymer 1 | Sodium lauryl ether sulfate 2 EO (water) polyglyceryl-4 isostearate (2 Me—THF) 10/90 | 91/9 | 10.8% |
| 9 | Polymer 1 | Sodium decyl sulfate (water) | 91/9 | 15% |
| 10 | Polymer 2 | Sodium N-lauroyl sarcosinate (water) | 97/3 | 24% |
| 11 | Polymer 3 | Sodium N-lauroyl sarcosinate (water) | 97/3 | 20% |
| (outside the invention) | Polymer 1 | Sodium dodecyl sulfate (water) | 91/9 | unstable |

Examples 12 to 17: Aqueous Dispersions with Cationic Surfactant System

| Example | Polymer | Surfactant system (put in solution in) | Polymer/ surfactant ratio | Solids content of the dispersion |
|---|---|---|---|---|
| 12 | Polymer 1 | Behenyltrimethylammonium chloride (water) | 91/9 | 21% |
| 13 | Polymer 1 | Cetrimonium chloride (water) | 97/3 | 26.5% |
| 14 | Polymer 1 | behenyl trimethyl ammonium chloride (water)/polyoxyethylenated sorbitan monopalmitate (20 EO) (water) (10/90) | 91/9 | 14% |
| 15 | Polymer 1 | cetrimonium chloride (water)/polyoxyethylenated sorbitan monopalmitate (20 EO) (water) (10/90) | 91/9 | 16% |
| 16 | Polymer 1 | cetrimonium chloride (water)/ polyglyceryl-4 isostearate (water) (10/90) | 91/9 | 26% |

Comparison Examples 18 to 22: Aqueous Dispersions with Non-Ionic Surfactant System

| Example | Polymer | Surfactant system (put in solution in) | Polymer/ surfactant ratio | Solids content of the dispersion |
|---|---|---|---|---|
| 18 | Polymer 1 | polyoxyethylenated sorbitan monopalmitate (2 Me THF) HLB = 15.3 | 91/9 | 18% |
| 19 | Polymer 1 | polyoxyethylenated lauryl alcohol (23 EO) (water)/ polyoxyethylenated lauryl alcohol (4 EO) (95/5) (2 MeTHF) HLB = 16 | 91/9 | 34% |
| 20 | Polymer 1 | polyoxyethylenated lauryl alcohol (23 EO) (water)/ polyoxyethylenated lauryl alcohol (4 EO) (2MeTHF) (80/20) HLB = 15.1 | 91/9 | 18.5% |

-continued

| Example | Polymer | Surfactant system (put in solution in) | Polymer/ surfactant ratio | Solids content of the dispersion |
|---|---|---|---|---|
| 21 (outside the invention) | Polymer 1 | polyoxyethylenated lauryl alcohol (4 EO) HLB = 10 (2 MeTHF) | 91/9 | unstable |
| 22 (outside the invention) | Polymer 1 | polyglyceryl-4 isostearate (2 Me—THF) HLB = 5 | 91/9 | unstable |

Preparation of the Dyeing Compositions

Invention: A dyeing composition was prepared from the dispersion 11 containing P3 as above described (15% active material dispersed in water), 6% of pigment (MICA (and) IRON OXIDES) and qs to 100% with isododecane Comparison1:

The following comparative composition was prepared with the same pigment used at the same concentration.

| Comparative composition 1 | Conc. |
|---|---|
| GLYCINE | 3% |
| PHENOXYETHANOL | 0.7% |
| DIVINYLDIMETHICONE/DIMETHICONE COPOLYMER (and) C12-13 PARETH-3 (and) C12-13 PARETH-23 (60% Active Material in an aqueous emulsion) | 8.3% |
| CAPRYLYL GLYCOL | 1% |
| MAGNESIUM ALUMINUM SILICATE | 1.1% |
| STYRENE/ACRYLATES/AMMONIUM METHACRYLATE COPOLYMER (and) SODIUM LAURETH SULFATE (and) CAPRYLYL GLYCOL (40% Active material in an aqueous emulsion 40%) | 21% |
| MICA (and) IRON OXIDES | 6% |
| water | q.s |

Comparison 2:

A comparative composition was prepared from a solution of P3 (15 active material in isododecane), 6% of pigment (MICA (and) IRON OXIDES) and qs 100% isododecane.

Evaluation of the Color Resistance

These dyeing compositions were applied on locks of natural hair with 90% of white hair. The compositions were applied on dried hair and on wet hair. 0.5 g of the dyeing composition was applied on 1 g of hair lock. After 24 h hours, the locks were rinsed with water and dried. Then the locks were shampooed and dried.

The color resistance was visually evaluated on washed dried hair and after 1 shampoo, 3 shampoos and 5 shampoos on dried hair according to a resistance evaluation scale ranging from 5 (high color resistance) to 1 (no color resistance).

The evaluation is summarized in the table below:

|  | Application | Water resistance | After 1 shampoo | After 3 shampoo | After 5 shampoo |
|---|---|---|---|---|---|
| Invention comp. | Dried hair | 5 | 5 | 4 | 3 |
|  | Wet hair | 5 | 5 | 3 | 1 |
| Comparative comp. 1 | Dried hair | 5 | 5 | 2 | 1 |
|  | Wet hair | 5 | 5 | 2 | 1 |
| Comparative comp. 2 | Dried hair | 5 | 5 | 2 | 1 |
|  | Wet hair | 5 | 5 | 2 | 1 |

These examples show that the composition of the invention provides an improvement of the color resistance to shampoos. After 5 shampoos, the color is still acceptable whereas with the comparative compositions 1 or 2, the locks are no more colored.

The invention claimed is:

1. A hair dyeing process comprising:
    applying an aqueous composition to hair;
    the aqueous composition comprising at least one pigment and at least one aqueous dispersion of supramolecular polyalkene polymer with a surfactant system selected from the group consisting of:
    1) a surfactant system comprising at least one anionic surfactant optionally combined with at least one non-ionic surfactant, with the exclusion of the surfactant system containing only dodecyl sulfate and/or an alkali metal salt of dodecyl sulfate;
    2) a surfactant system comprising at least one cationic surfactant, optionally combined with at least one non-ionic surfactant; and
    3) a surfactant system consisting of non-ionic surfactant(s) wherein the non-ionic surfactant has an HLB greater than 10 or the mixture of non-ionic surfactants has an HLB greater than 10.

2. The process according to claim 1, wherein the supramolecular polyalkene polymer can be obtained from the condensation of at least one polyalkene polymer functionalized with at least one reactive group, with at least one junction group functionalized with at least one reactive group that can react with the reactive group(s) of the functionalized polyalkene polymer, said junction group being capable of forming at least three hydrogen bonds.

3. The process according to claim 2, wherein the functionalized polyalkene polymer has the formula:

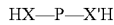

where XH and X'H are reactive groups, with X and X', which may be identical or different, are chosen from O, S, NH and $NR_a$, $R_a$ representing a linear or branched $C_1$-$C_6$ alkyl group; and P represents a homo- or copolymer that can be obtained by polymerization of one or more linear, cyclic and/or branched, mono- or polyunsaturated $C_2$-$C_5$ alkenes.

4. The process according to claim 3, wherein P represents a polyethylene, a polybutylene, a polybutadiene, a hydrogenated polybutadiene, a polyisoprene, a poly(1,3-pentadiene), a polyisobutylene, or copolymers thereof.

5. The process according to claim 3, wherein X=X'=O.

6. The process according to claim 2, wherein the functionalized junction group has the formula:

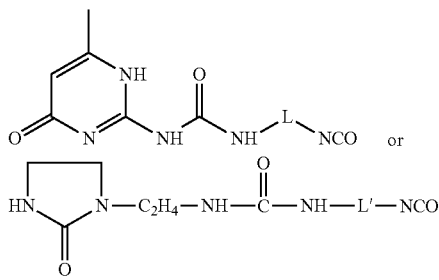

in which L and L' is a saturated or unsaturated, or aromatic, linear, cyclic and/or branched C1-C20 divalent alkylene carbon-based group, optionally comprising 1 to 4 N and/or O heteroatoms.

7. The process according to claim 6, wherein L and L' is a divalent substituent selected from the group consisting of phenylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), isophorone-, 4,4'-methylene bis(cyclohexylene), tolylene, 2-methyl-1,3-phenylene, 4-methyl-1,3-phenylene and 4,4-biphenylenemethylene.

8. The process according to claim 3, wherein the supramolecular polyalkene polymer is of the formula:

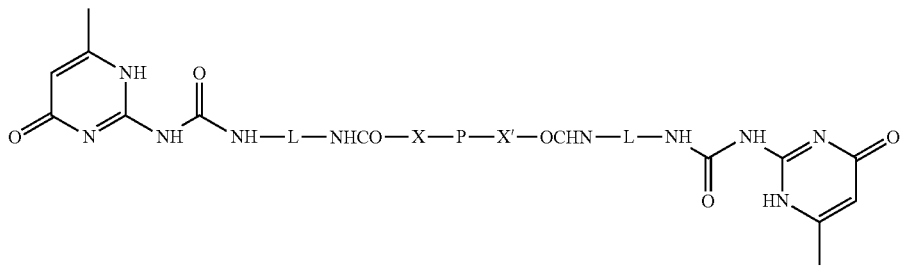

or formula (C2):

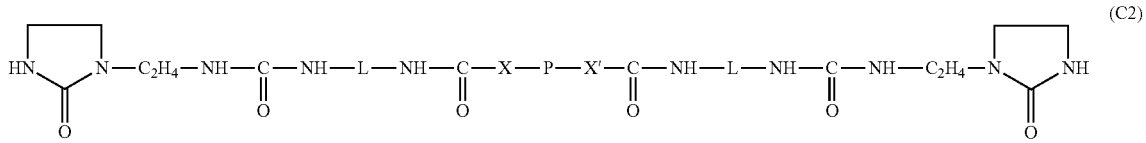

wherein P, X, X' having the meanings as defined in claim 3 and L is a saturated or unsaturated, or aromatic, linear, cyclic and/or branched C1-C20 divalent alkylene carbon-based group, optionally comprising 1 to 4 N and/or O heteroatoms.

9. The process according to claim 1, wherein
the surfactant system comprises at least one anionic surfactant, with the exclusion of the surfactant system containing only dodecyl sulfate and/or an alkali metal salt of dodecyl sulfate.

10. The process according to claim 1, wherein the surfactant system comprises at least one anionic surfactant and the at least one anionic surfactant is selected from the group consisting of sulfate surfactants, sulfonate surfactants, carboxylic surfactants, and mixtures thereof.

11. The process according to claim 1, wherein the surfactant system comprises at least one anionic surfactant and the at least one anionic surfactant is selected from the group consisting of:
acylglycinates, acyllactylates, acylsarcosinates, acylglutamates;
alkyl-D-galactosideuronic acids, alkyl ether carboxylic acids, alkyl(C6-30 aryl) ether carboxylic acids, alkylamido ether carboxylic acids; and the salts of these compounds; and
the alkyl and/or acyl groups of these compounds including from 6 to 30 carbon atoms, where these compounds may be polyoxyethylenated.

12. The process according to claim 1, wherein the surfactant system comprises at least one anionic surfactant and the at least one anionic surfactant is selected from the group consisting of:
alkyl sulfates, alkyl ether sulfates, alkylamido ether sulfates, alkylaryl polyether sulfates, monoglyceride sulfates; and the salts of these compounds; the alkyl groups of these compounds including from 6 to 30 carbon atoms; where these compounds may be polyoxyethylenated.

13. The process according to claim 1, wherein the surfactant system comprises a cationic surfactant.

14. The process according to claim 13, wherein the cationic surfactant is selected from the group consisting of quaternary ammonium salts having formula (Ia):

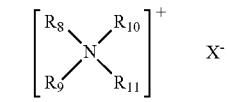

in which:
groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ including from 8 to 30 carbon atoms, it being possible for the linear or branched aliphatic groups to include heteroatoms, these heteroatoms not being adjacent, and halogens; and $X^-$ is an anion selected from the group consisting of halides, phosphates, acetates, lactates, $(C_1-C_4)$alkyl sulfates, $(C_1-C_4)$alkyl sulfonates; $(C_1-C_4)$alkylaryl sulfonates; $C_1-C_{30}$ alkyl, $C_1-C_{30}$ alkoxy, $(C_2-C_6)$ polyoxyalkylene, $C_1-C_{30}$ alkylamide, $(C_{12}-C_{22})$alkyl-$(C_2C_6)$alkylamido, $(C_{12}-C_{22})$alkyl acetate and $C_1-C_{30}$ hydroxyalkyl groups.

15. The process according to claim 1, wherein the surfactant system consists of non-ionic surfactant(s) wherein the non-ionic surfactant has an HLB greater than 10 or the mixture of non-ionic surfactants has an HLB greater than 10.

16. The process according to claim 1, wherein the surfactant system comprises non-ionic surfactant(s) and the non-ionic surfactant(s) is selected from the group consisting of:
    alcohols or alpha-diols, these compounds being polyethoxylated and/or polypropoxylated and/or polyglycerolated, the number of ethylene oxide and/or propylene oxide groups possibly ranging from 2 to 100, and the number of glycerol groups ranging from 2 to 30; these compounds comprising at least one fatty chain including from 8 to 30 carbon atoms;
    polyethoxylated fatty amides having from 2 to 30 ethylene oxide units;
    polyglycerolated fatty amides including on average from 1 to 5 glycerol groups;
    ethoxylated fatty acid esters of sorbitan having from 2 to 40 units of ethylene oxide;
    fatty acid esters of sucrose;
    polyoxyalkylenated fatty acid esters containing from 2 to 150 mol of ethylene oxide; and
    mixtures thereof.

17. The process according to claim 1, wherein the surfactant system comprises a non-ionic surfactant having an HLB greater than 10 which is selected from the group consisting of:
    cetyl alcohol polyoxyethylenated with 6 EO,
    cetyl alcohol polyoxyethylenated with 10 EO,
    cetyl alcohol polyoxyethylenated with 20 EO,
    cetyl alcohol polyoxyethylenated with 24 EO,
    lauryl alcohol polyoxyethylenated with 7 EO,
    lauryl alcohol polyoxyethylenated with 9 EO,
    lauryl alcohol polyoxyethylenated with 10 EO,
    lauryl alcohol polyoxyethylenated with 12 EO,
    lauryl alcohol polyoxyethylenated with 23 EO,
    stearyl alcohol polyoxyethylenated with 10 EO,
    stearyl alcohol polyoxyethylenated with 20 EO,
    stearyl alcohol polyoxyethylenated with 21 EO,
    polyoxyethylenated sorbitan monolaurate (4 EO),
    polyoxyethylenated sorbitan monolaurate (20 EO),
    polyoxyethylenated sorbitan monopalmitate (20 EO),
    polyoxyethylenated sorbitan monostearate (20 EO) and
    polyoxyethylenated sorbitan monooleate (20 EO).

18. The process according to claim 1, wherein the surfactant system further comprises a surfactant with HLB less than or equal to 10, and the surfactant with HLB less than or equal to 10 is selected from the group consisting of:
    cetyl alcohol polyoxyethylenated with 2 EO,
    lauryl alcohol polyoxyethylenated with 2 EO,
    lauryl alcohol polyoxyethylenated with 3 EO,
    lauryl alcohol polyoxyethylenated with 4 EO,
    stearyl alcohol polyoxyethylenated with 2 EO,
    sorbitan monostearate polyoxyethylenated with 4 EO and
    polyglyceryl-4 isostearate.

19. The process according to claim 1, wherein the surfactant system comprises polyoxyethylenated lauryl alcohol (4 EO) and polyoxyethylenated lauryl alcohol (23 EO).

20. The process according to claim 1, wherein the surfactant system comprises anionic surfactant and non-ionic surfactant selected from the group consisting of:
    polyoxyethylenated sorbitan monopalmitate (20 EO)/sodium decyl sulfate,
    polyoxyethylenated sorbitan monopalmitate (20 EO)/sodium N-lauroyl sarcosinate,
    Laurylethersulfate/polyoxyethylenated sorbitan monopalmitate (20 EO),
    Laurylethersulfate/polyglyceryl-4 isostearate and
    Laurylethersulfate/polyglyceryl-4 isostearate.

21. The process according to claim 1, wherein the surfactant system comprises cationic surfactant and non-ionic surfactant selected from the group consisting of:
    cetrimonium chloride/polyoxyethylenated sorbitan monopalmitate (20 EO),
    behenyl trimethylammonium chloride/polyoxyethylenated sorbitan monopalmitate (20 EO),
    cetrimonium chloride/polyglyceryl-4 isostearate, and
    behenyl trimethylammonium chloride/polyglyceryl-4 isostearate.

22. The process according to claim 1, wherein the supramolecular polyalkene polymer is present in a content ranging from 2% to 50% by weight relative to the total weight of the dispersion.

23. The process according to claim 1, wherein the surfactant system is present in a content ranging from 0.01% to 5% by weight, relative to the total weight of the dispersion.

24. The process according to claim 1, wherein the supramolecular polyalkene polymer and the surfactant system are present in the dispersion in a polymer/surfactant weight ratio ranging from 9 to 49.

25. The process according to claim 1, in which the pigment is present in an amount of between 0.5% and 40% by weight of the total weight of the aqueous composition.

* * * * *

UNITED STATES PATENT AND TRADEMARK OFFICE
CERTIFICATE OF CORRECTION

PATENT NO. : 10,973,751 B2
APPLICATION NO. : 16/500496
DATED : April 13, 2021
INVENTOR(S) : Chodorowski-Kimmes Page 1 of 1

It is certified that error appears in the above-identified patent and that said Letters Patent is hereby corrected as shown below:

In the Claims

In Column 43, Claim 14, Lines 1-2, delete "group such as aryl or alkylaryl," and insert -- group, --, therefor.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*